(12) United States Patent
Surmeier et al.

(10) Patent No.: US 7,629,323 B2
(45) Date of Patent: Dec. 8, 2009

(54) MANIPULATION OF NEURONAL ION CHANNELS

(75) Inventors: D. James Surmeier, Chicago, IL (US); Tatiana Tkatch, Chicago, IL (US); Gytis Baranauskas, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/761,557

(22) Filed: Jan. 21, 2004

(65) Prior Publication Data

US 2004/0220082 A1 Nov. 4, 2004

Related U.S. Application Data

(60) Provisional application No. 60/441,375, filed on Jan. 21, 2003.

(51) Int. Cl.
*C07H 21/04* (2006.01)
(52) U.S. Cl. ............. 514/44; 536/24.31; 536/24.5; 536/24.1
(58) Field of Classification Search ............... 435/91.1, 435/91.3, 325, 375; 514/44; 536/24.5, 24.3, 536/24.31, 24.33
See application file for complete search history.

(56) References Cited

U.S. PATENT DOCUMENTS 6,071,891 A * 6/2000 Low et al. ............ 514/44

FOREIGN PATENT DOCUMENTS

WO WO 02/44321 * 6/2002

OTHER PUBLICATIONS

Paroo et al. Challenges for RNAi in vivo. Trends in Biotechnology (2004), vol. 22(8) 390-394. Elsevier.*
Caplen NJ. RNAi as a Gene Therapy Approach. Expert Opinon. Biol. Thera. (2003) vol. 3(4) 575-586. Ashley Publications Ltd.*
Adams, A. RNA therapeutics enter clinical trials. Scientist (2005), vol. 19:Issue 1. Institute for Scientific Information.*
Green et al. Antisense oligonucleotides: an evolving technology for the modulation of gene expression in human disease. J Am Coll Surg (2000), vol. 191: 93-105. Elsevier.*
Jen et al. Suppresion of Gene Expression by Targeted Disruption of Messenger RNA: Available Options and Current Strategies. Stem Cells (2000), vol. 18:307-319. AlphaMed Press.*
Novina et al. The RNAi Revolultion. Nature 2004, vol. 430: 161-164. Nature Publishing Group.*
Hammond et al. Post-transcriptional gene silencing by double-stranded RNA Nature Reviews, 2001, vol. 2, 110-119. MacMillan Magazines Ltd.*
Chang et al. The increase of voltage-gated potassium channel Kv3.4 mRNA expression in oral squamous cell carcinoma. J Oral Pathol Med. 2003, vol. 32: 606-11.*

Tkatch et al. Kv3.4 KChannels may be responsible for spike broadening during burst firing in Globus Pallidus neurons. Society for Neuroscience, 1999, vol. 25: 179.17.*
Rudy, B. & McBain, C. J. TINS 24, 517-26 (2001).
Coetzee, W. A. et al., Ann N Y Acad Sci 868, 233-85 (1999).
Brew, H. M. & Forsythe, I. D. J Neurosci 15, 8011-22 (1995).
Du, J., Zhang, L., Weiser, M., Rudy, B. & McBain, C. J., Neurosci 16, 506-18 (1996).
Lenz, S., Perney, T. M., Qin, Y., Robbins, E. & Chesselet, M. F., Synapse 18, 55-66 (1994).
Weiser, M. et al., J Neurosci 14, 949-72 (1994).
Weiser, M. et al., J Neurosci 15, 4298-314 (1995).
Martina, M., Schultz, J. H., Ehmke, H., Monyer, H. & Jonas, P., J Neurosci 18, 8111-25 (1998).
Baranauskas, G., Tkatch, T. & Surmeier, D. J.. J Neurosci 19, 6394-404 (1999).
Erisir, A., Lau, D., Rudy, B. & Leonard, C. S., J Neurophysiol 82, 2476-89 (1999).
Wigmore, M. A. & Lacey, M. G., J Physiol 527 Pt 3, 493-506 (2000).
Schroter, K. H. et al., FEBS Lett 278, 211-6 (1991).
Rettig, J. et al., Embo J 11, 2473-86 (1992).
Diochot, S., Schweitz, H., Beress, L. & Lazdunski, M., J Biol Chem 273, 6744-9 (1998).
Thompson, S., J Gen Physiol 80, 1-18 (1982).
Song, W. J. et al., J Neurosci 18, 3124-37 (1998).
Kofuji, P., Davidson, N. & Lester, H. A., Proc Natl Acad Sci U S A 92, 6542-6 (1995).
Sheng, M., Liao, Y. J., Jan, Y. N. & Jan, L. Y., Nature 365, 72-5 (1993).
Wang, H. S. et al., Science 282, 1890-3 (1998).
Abbott, G. W. et al., Cell 104, 217-31 (2001).
Macica, C. M. & Kaczmarek, L. K., J Neurosci 21, 1160-8 (2001).
Murakoshi, H., Shi, G., Scannevin, R. H. & Trimmer, J. S., Mol Pharmacol 52, 821-8 (1997).
Rettig, J. et al., Nature 369, 289-94 (1994).
Surmeier, D. J., Bargas, J., Hemmings, H. C., Jr., Nairn, A. C. & Greengard, P., Neuron 14, 385-97 (1995).
Hamill, O. P., Marty, A., Neher, E., Sakmann, B. & Sigworth, F. J., Pflugers Arch 391, 85-100 (1981).
Yan, Z. & Surmeier, D. J., J Neurosci 16, 2592-604 (1996).
Tkatch, T., Baranauskas, G. & Surmeier, D. J., Neuroreport 9, 1935-9 (1998).
Rhodes, K. J. et al., J Neurosci 17, 8246-58 (1997).

* cited by examiner

*Primary Examiner*—Kimberly Chong
(74) *Attorney, Agent, or Firm*—Casimir Jones, S.C.

(57) ABSTRACT

The present invention provides compositions and methods for the manipulation of ion channels. For example, the present invention relates to Parkinson's and other neurological diseases and conditions, and treatments thereof. In particular, the present invention provides methods of decreasing pathophysiological high frequency neuronal bursts of Parkinson's and other neurological diseases and conditions. Methods of the present invention comprise decreasing Kv3 ion channel activity in fast-spiking neurons, including by decreasing activity of a Kv3.4 protein and by specifically targeting a Kv3.4 protein with an inhibitor.

8 Claims, No Drawings

SEQUENCE LISTING

```
<160> NUMBER OF SEQ ID NOS: 5

<210> SEQ ID NO 1
<211> LENGTH: 19
<212> TYPE: DNA
<213> ORGANISM: Rattus rattus

<400> SEQUENCE: 1
gcgaaatgtg acggagatc                                                 19

<210> SEQ ID NO 2
<211> LENGTH: 19
<212> TYPE: DNA
<213> ORGANISM: Rattus rattus

<400> SEQUENCE: 2
ggaaacgagc agactccaa                                                 19
```

-continued

```
<210> SEQ ID NO 3
<211> LENGTH: 19
<212> TYPE: DNA
<213> ORGANISM: Rattus rattus

<400> SEQUENCE: 3
gcagaatggt gacgctaat                                                   19

<210> SEQ ID NO 4
<211> LENGTH: 19
<212> TYPE: DNA
<213> ORGANISM: Rattus rattus

<400> SEQUENCE: 4
ggcagtgttg agccgaaac                                                   19

<210> SEQ ID NO 5
<211> LENGTH: 19
<212> TYPE: DNA
<213> ORGANISM: Rattus rattus

<400> SEQUENCE: 5
cagccacttc gactatgac                                                   19
```

MANIPULATION OF NEURONAL ION CHANNELS

The present application claims priority to U.S. Provisional Patent Application Ser. No. 60/441,375, filed Jan. 21, 2003, the disclosure of which is herein incorporated by reference in its entirety.

The present application was funded in part with government support under grant number PO1 ns-26473 from the National Institutes of Health National Institute of Neurological and Stroke Disease. The government may have certain rights in this invention.

FIELD OF THE INVENTION

The present invention provides compositions and methods for the manipulation of ion channels. For example, the present invention relates to Parkinson's and other neurological diseases and conditions, and treatments thereof. In particular, the present invention provides methods of decreasing pathophysiological high frequency neuronal bursts of Parkinson's and other neurological diseases and conditions.

BACKGROUND OF THE INVENTION

Parkinson's disease (PD) is a progressive disorder of the central nervous system affecting over 1 million people in the United States. Clinically, the disease is characterized by a decrease in spontaneous movements, gait difficulty, postural instability, rigidity and tremor. Both men and women are affected. The frequency of the disease is considerably higher in individuals over age 50, even though there is an alarming increase of patients of younger age. Due to the increased life expectancy in this country and worldwide, an increasing number of people will be victims of Parkinson's disease.

The major symptoms of the disease were originally described in 1817 by an English physician, Dr. James Parkinson, who called it "Shaking Palsy". It was not until the 1960's, however, that pathological and biochemical changes in the brain of patients were identified, leading to treatments of the disease opening the way to the first effective medication for the disease.

Parkinson's disease is caused by the degeneration of the pigmented neurons in the Substantia Nigra of the brain, resulting in decreased dopamine availability. Treatment has been directed to increasing the amount of dopamine availability, or to removing the degenerated neurons, and include both medication and surgical treatment.

Medication, including the administration of the drug levodopa, has been the standard treatment for Parkinson's disease. Levodopa is a dopamine precursor, a substance that is transformed into dopamine by the brain. Once it reaches the brain, levodopa is converted to dopamine which replaces the same substance not present in sufficient amounts in Parkinson's patients. The prescription of high dosages of levodopa was the first dramatic breakthrough in the treatment of PD. Treatment with levodopa does not, however, prevent the progressive changes of the brain typical of Parkinson's disease. The drug may also produce side effects in some people, due to its change to dopamine before reaching the brain. Thus, patients experienced debilitating side effects, including severe nausea and vomiting.

The simultaneous administration with levodopa of substances inhibiting this change allows a higher concentration of levodopa to reach the brain and also considerably decreases the side effects. For example, levodopa/carbidopa (Sinemet) represented a significant improvement. The addition of carbidopa prevents levodopa from being metabolized in the gut, liver and other tissues, and allows more of it to get to the brain. Therefore, a smaller dose of levodopa is needed to treat symptoms, and the unpleasant side effects are greatly reduced, though not absent.

Some new drugs have recently been approved offering a wider choice of medications for the patient. For example, Symmetrel (amantadine hydrochloride), originally an anti-flu medication, is though to work in PD by either blocking the reuptake of dopamine or by increasing the release of dopamine by neurons, thereby increasing the supply of dopamine in the synapses. It is thus called an indirect-acting dopamine agonist, and is widely used as an early monotherapy, with the more powerful Sinemet added when needed. When its benefits seem to lessen, stopping the drug for a short period and then reintroducing it seems to again provide efficacy, according to some clinicians.

Selegiline or deprenyl (Eldepryl) has been shown to delay the need for Sinemet when prescribed in the earliest stage of PD, and has also been approved for use in later stages to boost the effects of Sinemet. Dopamine agonists are drugs that activate the dopamine receptor directly, and can be taken alone or in combination with Sinemet. Agonists available in the United States include bromocriptine (Parlodel), pergolide (Permax), pramipexole (Mirapex) and andropinirole (Requip).

COMT inhibitors such as tolcapone (Tasmar) and entacapone (Comtan), represent a new class of Parkinson's medications. These drugs must be taken with levodopa. They prolong the duration of symptom relief by blocking the action of an enzyme which breaks down levodopa before it reaches the brain.

Other drugs include anticholinergics (trihexyphenidyl, benztropine mesylate, procyclidine, etc.), which do not act directly on the dopaminergic system. Instead they act to decrease the activity of the balancing neurotransmitter, acetylcholine. Since it is known that PD relates primarily to decreased activity of dopamine, one avenue of treatment has been to decrease the cholinergic system to equal that of the dopaminergic system. Most effective in the control of tremor, these drugs may be contraindicated in certain older patients since they tend to cause confusion and hallucination.

Unfortunately, all of the medications currently available exhibit undesirable side effects. Like the symptoms of PD itself, the side effects caused by Parkinson's medications vary from patient to patient. They may include dry mouth, nausea, dizziness, confusion, hallucinations, drowsiness, insomnia, and other unwelcome symptoms. Some patients experience no side effects from a drug, while others have to discontinue its use because of them.

Thus, other treatments involve surgical intervention. One widely utilized surgical procedure is a pallidotomy. This procedure has a long history in the treatment of Parkinson's disease, but it fell out of favor with the advent of levodopa. In recent years it has gained new popularity, mainly because magnetic imaging now allows it to be performed with far greater precision. Pallidotomy is indicated for patients who have developed dyskinetic movements in reaction to their medications. It targets the source of these unwanted movements, the globus pallidus, and uses an electrode to destroy the trouble-causing cells. As with any surgical procedure, there are risks involved. The most serious is the possibility of stroke; other risks include partial loss of vision, speech and swallowing difficulties, and confusion, as well as the general risks associated with surgery.

A related procedure is deep brain stimulation. Like pallidotomy, this technique also seeks to stop uncontrollable movements. It is based on the technology of cardiac pacemakers. Electrodes are implanted in the thalamus or globus pallidus and connected to a pacemaker-like device, which the patient can switch on or off as symptoms dictate.

All of the treatments described above suffer from drawbacks, some serious, which debilitate the patient and compromise the quality of life. Moreover, none of these treatments provide a cure for the disease. Thus, what is needed are treatments that alleviate the symptoms of PD without disrupting normal neuronal functioning. Preferably, such treatments would also affect a cure of PD.

SUMMARY OF THE INVENTION

The present invention relates to Parkinson's and other neurological diseases and conditions, and treatments therefore. In particular, the present invention provides methods of decreasing pathophysiological high frequency neuronal bursts of Parkinson's and other neurological diseases and conditions.

Thus, the present invention provides methods of inhibiting the ability of a fast-spiking neuronal cell to discharge at a high rate, comprising providing a toxin or other inhibitor (e.g., small molecule drug, antibody, etc.) directed against Kv3.4 subunits (e.g., Kv3.4a, Kv3.4b, etc.) to the cell that has Kv3 channels comprising a Kv3.4 subunit, such that the high rate of discharge is inhibited. In some embodiments, the cell is a globus pallidus neuron, a hippocampal interneuron, or a subthalamic neuron. In other embodiments, the cell is a neuron of the cerebral cortex, hippocampus, or those involved in the auditory pathway. The present invention includes any fast-spiking neuronal cell and is not limited to any particular cell class or region of the nervous system. In more particular embodiments, the cell is a parvalbumin-expressing GABAergic, globus pallidus neuron, a parvalbumin-expressing GABAergic CA1 hippocampal interneuron, or a glutamatergic subthalamic neuron. In some further embodiments, the cell is in vitro; in other further embodiments, the cell is in vivo.

In other embodiments, the present invention provides methods of manipulating neuronal ion channels, comprising transfecting a fast-spiking neuronal cell with a vector encoding an siRNA directed against an mRNA encoding a Kv3.4 protein (e.g., Kv3.4a) and capable of expression in the cell, such that expression of the Kv3.4 protein is decreased, and properties of Kv3 ion channels are altered. In some embodiments, the cell is in vitro; in other further embodiments, the cell is in vivo.

In yet other embodiments, the present invention provides methods of inhibiting the ability of a fast-spiking neuronal cell to discharge at high rates, comprising transforming the cell with a vector encoding an siRNA directed against a gene encoding a Kv3.4 protein (e.g., Kv3.4a) and capable of expression in the cell, such that expression of the Kv3.4 protein is decreased, and the ability of the neuronal cell to discharge at high rates is inhibited.

In yet other embodiments, the present invention provides methods of inhibiting the ability of a fast-spiking neuronal cell to discharge at a high rate, comprising transfecting a fast-spiking cell with a vector encoding a gene encoding a toxin directed against Kv3.4 subunits and capable of expression in the cell, such that the toxin is expressed, and the ability of the neuronal cell to discharge at high rates is inhibited. In some embodiments, the cell expresses a Kv3.4a subunit; in other embodiments, the toxin is directed against Kv3.4a. In some embodiments, the encoded toxin is BDS-1.

In other embodiments, the present invention provides methods of inhibiting the ability of a fast-spiking neuronal cell to discharge at a high rate, comprising transfecting a central nervous system cell with a vector encoding a gene encoding a toxin directed against Kv3.4 subunits and capable of expression in the cell, and placing the transfected cell near a fast-spiking neuronal cell capable of a high discharge rate and which has Kv3 channels comprising a Kv3.4a subunit, such that the toxin is expressed and the ability of the neuronal cell to discharge at high rates is inhibited.

The present invention also provides methods for screening for compounds that bind to a Kv3.4 protein (e.g., Kv3.4a), comprising providing a Kv3.4 protein, and a test compound; and detecting binding of the compound to the Kv3.4 protein. In some embodiments, the methods further comprise screening compounds identified as binding to Kv3.4 protein for the ability to specifically interfere with Kv3 channel function as described below.

The present invention also provides methods for screening for compounds that specifically interfere with Kv3 channel function where the Kv3 channels comprise the Kv3.4 subunit (e.g., Kv3.4a), comprising contacting a cell expressing homomeric Kv3.4 channels with a test compound and measuring the resulting ion channel currents.

The present invention also provides methods for screening for compounds that specifically interfere with Kv3 channel function where the Kv3 channels comprise the Kv3.4 subunit (e.g., Kv3.4a), comprising contacting a fast-spiking cell expressing Kv3 channels with a test compound, and measuring the resulting spikes.

In some embodiments, subjects (e.g., research animals, patients, etc.) are treated with a compound or method of the present invention to characterize, alter, or treat (e.g., ameliorate one or more symptoms) a neurological condition or phenomena, including, but not limited to, Parkinson's disease, epilepsy, hearing (e.g., tonal discrimination, high frequency tonal discrimination), memory, learning, and hearing, memory, and learning disorders.

Definitions

To facilitate an understanding of the present invention, a number of terms and phrases as used herein are defined below:

The term "fast-spiking" (FS) when used to describe a class of neurons refers to the capacity of the neurons to discharge at high rates for long periods with little spike frequency adaptation or attenuation in spike height. Thus, these neurons are capable of sustained high frequency (greater than about 100 Hz, or greater than about 150 Hz) discharge without significant accommodation. This property of FS neurons is attributable in large measure to their expression of fast delayed rectifier channels, in other words, channels that activate and deactivate very quickly.

The term "pathophysiological fast-spiking" when used in reference to Parkinson's disease refers to neuronal spiking in high frequency bursts. One measurement is the percentage of time a neuron spends discharging at high frequency (greater than about 150 Hz); for example, in Parkinson's disease patients, and in animal models of Parkinson's disease, subthalamic nucleus neurons spend a higher than normal amount percentage of the time in his high frequency mode.

The term "physiological fast-spiking" when used in reference to fast-spiking neurons refers to fast-spiking which occurs in normal functioning of the brain.

The term "Kv3" refers to a subfamily of depolarization-activated, $Ca^{2+}$-independent $K^+$ channels. The members within this family can form either momomeric or heteromeric functional tetrameric channels. Mammalian neurons create diversity of channel function by coexpression of members of different Kv subfamilies, coexpression of multiple members of a Kv subfamily, and coexpression of multiple principal and auxiliary subunits. Kv3 genes appear to code for subunits that assemble into delayed rectifier channels.

The Kv3 subfamily of K+ channels are characterized by positively shifted voltage dependencies and very fast deactivation rates. Thus, all Kv3 currents activate relatively fast at voltages more positive than −10 mV. These properties are adaptations that allow these channels to produce currents that can specifically enable fast repolarization of action potentials without compromising spike initiation or height. The activation voltage and fast deactivation rates are believed to allow these channels to help repolarize action potentials fast without affecting the threshold for action potential generation. The fast deactivating current generates a quick recovery after hyperpolarization, thus maximizing the rate of recovery of Na+ channel inactivation without contributing to an increase in the duration of the refractory period. The short spike duration and rapid deactivation of the Kv3 currents after spike repolarization maximize the quick recovery of resting conditions after an action potential.

Several neurons in the mammalian central nervous system have incorporated into their repertoire of voltage-dependent conductances a relatively large number of Kv3 channels to enable repetitive firing at high frequencies, which ability crucially depends on the specific properties of Kv3 channels and their impact on excitability. Thus, the properties of the Kv3 channels are believed to contribute to the ability of neurons to fire at high frequencies and to help regulate the fidelity of synaptic transmission.

Four mammalian Kv3 genes have been identified, each of which generates, by alternative splicing, multiple protein products differing in their C-terminal sequences. These four genes are Kv3.1, Kv3.2, Kv3.3, and Kv3.4. Members of this class are known to co-assemble.

The term "Kv3.4" refers to a gene of a Kv3 K+ ion channel family. Products of the Kv3.4 genes in heterologous expression systems express A-type currents.

The terms "Kv3.4a", "Kv3.4c" and the like refer to splice variants of the Kv3.4 gene.

The term "heteromeric" when used in reference to an ion channel, refers to an assembly of an ion channel, where the subunits of the ion channel are the same.

The term "homomeric" when used in reference to an ion channel refers to an assembly of an ion channel, where at least one of the subunits of the channel are not the same.

The term "BDS-1" refers to blood depressing substance obtained from sea anemone *Anemonia sulcata* venom and described in Diochot, S (1998) J Biol Chem 273(12): 6755-9. The venom is a specific blocker for the rapidly inactivating Kv3.4 channel, and is a 43 amino acid long protein. In COS-transfected cells, BDS-I inhibits the Kv3.4 current in a reversible manner with an IC50 value of 47 nM. The specificity of the inhibition is demonstrated by the observations that BDS-I failed to block other K+ channels in the Kv1, Kv2, Kv3, and Kv4 subfamilies. Inward rectifier K+ channels are also insensitive to BDS-I.

As used herein, the term "transplant" refers to tissue used in grafting, implanting, or transplanting, as well as the transfer of tissues from one part of the body to another, or the transfer of tissues from one individual to another, or the introduction of biocompatible materials into or onto the body.

The term "transplantation" refers to the grafting of tissues from one part of the body to another part, or to another individual.

As used herein, the term "host" refers to any animal (e.g., warm blooded mammal), including, but not limited to, humans, non-human primates, rodents, and the like, which is to be the recipient of a particular treatment. Typically, the terms "host" and "patient" are used interchangeably herein in reference to a human subject.

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, aves, etc.

The term "biologically active," as used herein, refers to a protein or other biologically active molecules (e.g., catalytic RNA) having structural, regulatory, or biochemical functions of a naturally occurring molecule.

The term "biologically active agent" or "therapeutic agent" refers to an agent that possesses an activity or property capable of affecting or effecting a biochemical function, such as a structural (for example, binding ability) or regulatory activity or a reaction. Biochemical functions include but are not limited to physiological, genetic, cellular, tissue, and organismal activities. Moreover, as used herein, the term "agent" refers to biologically active agents and therapeutic agents, except where noted otherwise. Biological activities include activities associated with biological reactions or events in a subject or patient; preferably such activities can be detected, monitored, characterized, or measured.

The term "agonist," as used herein, refers to a molecule which, when interacting with an biologically active molecule, causes a change (e.g., enhancement) in the biologically active molecule or multi-molecular complex in which the biologically active molecule is present, which modulates the activity of the biologically active molecule or complex, resulting in increased activity. Agonists may include proteins, nucleic acids, carbohydrates, or any other molecules that bind or interact with biologically active molecules. For example, agonists can alter the activity of gene transcription by interacting with RNA polymerase directly or through a transcription factor. An increase in activity is an increase of at least about 10 percent, at least about 20 percent, at least about 50 percent, or at least about 100 percent, compared to the activity in the absence of the agonist.

The terms "antagonist" or "inhibitor," as used herein, refer to a molecule which, when interacting with a biologically active molecule, blocks or modulates the biological activity of the biologically active molecule or multi-molecular complex in which the biologically active molecule is present, resulting in decreased activity of the molecule or complex. Antagonists and inhibitors may include proteins, nucleic acids, carbohydrates, or any other molecules that bind or interact with biologically active molecules. Inhibitors and antagonists can effect the biology of entire cells, organs, or organisms (e.g., an inhibitor that slows tumor growth). A decrease in activity is a decrease of at least about 10 percent, at least about 20 percent, at least about 50 percent, or at least about 100 percent, compared to the activity in the absence of the antagonist or inhibitor. The term "toxin" is used interchangeably with the terms "antagonist" or "inhibitor," when used in reference to decreasing the activity of a biologically active molecule. An antagonist is "directed against" the molecule which it inhibits.

The term "modulate," as used herein, refers to a change in the biological activity of a biologically active molecule. Modulation encompasses increases and decreases in activity, a change in binding characteristics, or any other change in the biological, functional, or immunological properties of biologically active molecules. The term "manipulate" is used interchangeably with the term "modulate."

The term "therapeutically effective amount" is a functional term referring to an amount of material needed to make a qualitative or quantitative change in a clinically measured parameter for a particular subject. For example, prior to administration, the subject may exhibit at least one measurable symptom of disease or response to injury (for example, pulmonary congestion and/or difficulty breathing; evidence of hepatitis, or decrease in liver function; evidence or kidney inflammation or decrease in kidney function; etc), which upon administration of a therapeutically effective amount the measurable symptom is found to have changed. A therapeutically relevant effect relieves to some extent one or more symptoms of a disease or condition or returns to normal either partially or completely one or more physiological or biochemical parameters associated with or causative of the disease. In particular, the term "therapeutically effective amount" refers to an amount sufficient to reduce by a least about 15 percent, preferably by at least 50 percent, more preferably by at least 90 percent, and most preferably prevent, a clinically significant deficit in the activity, function, and/or response of a host. Alternatively, a therapeutically effective amount is sufficient to cause an improvement in a clinically significant condition in a host.

The term "therapeutically effective time" refers to the period of time during which a therapeutically effective amount of a therapeutic agent or biologically active agent is administered sufficient to prevent the onset or to shorten the course or severity of or to reverse the effects of a disease.

The term "biologically effective amount" is a functional term referring to an amount of material needed to make a qualitative or quantitative change in a biological activity of a particular subject; such activities include but are not limited to enzyme activities, production of antigen, and clearance of analyte from serum.

As used herein, the term "carrier" refers to a diluent, adjuvant, excipient, or vehicle with which a compound is administered. Such pharmaceutical carriers can be sterile liquids, such as water and oils, including those of petroleum, animal, vegetable, or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

As used herein, the term "gene targeting" refers to the alteration of genes through molecular biology techniques. Such gene targeting includes, but is not limited to, generation of mutant genes and knockout genes through recombination. When a gene is altered such that its product is no longer biologically active in a wild-type fashion, the mutation is referred to as a "loss-of-function" mutation. When a gene is altered such that a portion or the entirety of the gene is deleted or replaced, the mutation is referred to as a "knockout" mutation.

The term "antisense" when used in reference to DNA refers to a sequence that is complementary to a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-30 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule.

The term "ds siRNA" refers to a siRNA molecule that comprises two separate unlinked strands of RNA that form a duplex structure, such that the siRNA molecule comprises two RNA polynucleotides.

The term "hairpin siRNA" refers to a siRNA molecule that comprises at least one duplex region where the strands of the duplex are connected or contiguous at one or both ends, such that the siRNA molecule comprises a single RNA polynucleotide. The antisense sequence, or sequence which is complementary to a target RNA, is a part of the at least one double stranded region.

As used herein, the term "gene transfer system" refers to any means of delivering a composition comprising a nucleic acid sequence to a cell or tissue. For example, gene transfer systems include, but are not limited to vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system"

refers to gene transfer systems comprising viral elements (e.g., intact viruses and modified viruses) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule including, but not limited to DNA or RNA. The term encompasses sequences that include any of the known base analogs of DNA and RNA.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene encoding a factors that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are also distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed). Heterologous genes may be introduced into hematopoietic stem cells through molecular biology manipulation. The coding sequence of the heterologous gene is operatively linked to an expression control sequence. Generally a heterologous gene is first placed into a vector.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the terms "nucleic acid molecule encoding," "DNA sequence encoding," "DNA encoding," and the like refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5'end" if its 5' phosphate is not linked to the 3' oxygen of a mononucleotide pentose ring and as the "3'end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S. D. Voss et al, Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1 gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., *Molecular Cloning: A Laboratory Manual*, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target. The term "identity" or "similarity" and the like may be used interchangeably with "homology" and the like when used to refer to nucleic acid and amino acid sequences.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition below for "stringency").

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

The term "purified" refers to molecules, for example, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes.

The term "transient transfectant" refers to cells that have taken up foreign DNA but have failed to integrate this DNA. The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene that is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., *Molecular Cloning: A Laboratory Manual*, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. These examples are not to be construed as limiting the sample types applicable to the present invention.

DESCRIPTION OF THE INVENTION

The present invention provides compositions and methods for the manipulation of ion channels. For example, the present invention relates to Parkinson's and other neurological diseases and conditions, and treatments thereof. In particular, the present invention provides methods of decreasing pathophysiological high frequency neuronal bursts of Parkinson's and other neurological diseases and conditions.

In Parkinson's disease, the activity of globus pallidus and subthalamic nucleus neurons is abnormal. Neurons begin to discharge in high frequency bursts. The high frequency spiking in neurons is enabled by potassium selective ion channels composed of Kv3 family subunits. These channels are unique in that they activate quickly at membrane potentials only encountered during spiking. Moreover, they deactivate quickly. The net consequences of this behavior are that spikes are brief (minimizing alterations in other channels contributing to spiking) and, following termination of the spike, neurons are allowed to rapidly repolarize to spike threshold.

Current treatments for Parkinson's disease include those aimed at lesioning (which burn out regions of the brain) or functionally inactivating of these neurons with deep brain stimulation (which by electrical stimulation of a particular area inactivate neurons in that area). However, these treatments are irreversible (such as in lesioning) or require an in-dwelling electrode (as in deep brain stimulations). Moreover, the treated brain regions also play a role in normal movement control, as for example providing lubricating signals to the rest of the basal ganglia. Thus, although both treatments remove the pathophysiology of Parkinson's disease, in that they relieve the symptoms of the disease, these treatments also disrupt normal functioning of these neurons, leading to undesirable and debilitating side effects and symptoms.

Neurons with the capacity to discharge at high rates, designated fast-spiking (FS) neurons, are critical participants in central motor and sensory circuits. They are also the neurons which exhibit pathological behavior in Parkinson's disease. It is widely accepted that $K^+$ channels having Kv3.1 or Kv3.2 subunits underlie fast delayed rectifier currents that endow neurons with this FS ability. However, expression of these subunits in heterologous systems yield channels that activate at significantly more depolarized potentials than native Kv3 family channels, suggesting that channels comprised of Kv3.1 or Kv3.2 expressed in heterologous systems differ from native Kv3 family channels.

Experiments conducted during the development of the present invention have unexpectedly discovered that native channels incorporate a subunit that modifies gating. These experiments examined the possibility that native channels are heteromeric and contain subunits not found in heterologous systems. Four members of the Kv3 class, Kv3.1, 3.2, 3.3 and 3.4, are known to co-assemble. It was discovered that the incorporation of a splice variant of the Kv3.4 subunit, Kv3.4a, transforms Kv3.1 channels in heterologous expression systems, giving the Kv3.1 channels gating properties very similar to those found in FS neurons. Thus, co-expression of this splice variant with Kv3.1 subunits in HEK293 cells yield $K^+$ currents that strongly resemble those found in FS neurons, indicating that assembly of these subunits is sufficient to mimic native channels. Moreover, the Kv3.4 subunit was surprisingly and unexpectedly discovered to be expressed in FS neurons, but not in non-FS neurons. Moreover, molecular, electrophysiological and pharmacological studies indicate that a splice variant of the Kv3.4 subunit, Kv3.4a, co-assembles with Kv3.1 subunits in brain FS neurons. This coassembly increases the efficiency of the Kv3 channels in promoting spike repolarization and repetitive firing.

Thus, it was discovered that neurons having the ability to discharge at high rates, like those in the globus pallidus (GP) and subthalamic nucleus (STN) and others, express a unique $K^+$ channel that enables this behavior. These Kv3 family channels activate quickly during the upstroke of the spike, keep the spike brief and then deactivate quickly to allow the generation of the next spike. There are four known members of the Kv3 class: Kv3.1, Kv3.2, Kv3.3 and Kv3.4. It was discovered that these subunits form heteromeric channel complexes, and that the inclusion of a particular splice variant of the Kv3.4 subunit, Kv3.4a, dramatically increases the efficiency of heteromeric Kv3 channels in spike repolarization. Surprisingly, Kv3.4a mRNA is only expressed in fast-spiking neurons.

Most of the fast-spiking neurons that have been studied in the brain are interneurons that are sparsely distributed in the cortex and hippocampus. It was discovered that the only projection neurons that seem to express this subunit are in the output nuclei of the basal ganglia: globus pallidus (GP), subthalamic nucleus (STN) and to a lesser extent the substantia nigra pars reticulata. These are the nuclei that display the most pronounced pathophysiology in Parkinson's disease. This pathophysiology is characterized by high frequency bursts of spikes, precisely the sort of behavior enabled by Kv3.4a containing K+ channels.

These unexpected discoveries described above provide a method to treat Parkinson's disease and other neurological diseases and conditions. For example, one of these methods comprises selectively suppressing the aberrant discharge behavior in the small population of neurons involved in the disease or condition, without affecting the function of other nearby cells. Because the gene encoding Kv3.4a appears to be expressed only in those cells exhibiting the pathological discharge behavior, silencing this gene would not affect the function of other nearby cells. Moreover, even the cells exhibiting the pathological discharge behavior are able to assemble Kv3 channels with another subunit, which, although they may not be as efficient, as these channels appear to discharge more slowly, should still be sufficient to allow the targeted cells to function somewhat normally.

Thus, down-regulating Kv3.4a mRNA and protein is contemplated to eliminate the high frequency (e.g., pathological) discharge of these neurons without totally disrupting their normal function by diminishing the repolarizing efficiency of Kv3 channels. This will not disrupt the ability of STN neurons to respond to synaptic input or to generate patterned output. It will simply eliminate the pathophysiological bursts.

Thus, disruption of the function of Kv3 channel comprising the Kv3.4 subunit (e.g., Kv3.4a) is contemplated to eliminate the abnormal high frequency discharge associated with the pathophysiology of Parkinson's disease without damaging the brain, and thus allowing normal lower frequency neuronal discharge. Moreover, disruption of Kv3.4 subunit expression and/or channel function is contemplated to have therapeutic benefits of current therapies without the unwanted side effects accompanying complete disruption of the nuclei. In some embodiments, the methods of the present invention are used in conjunction with current therapies.

It is further contemplated that disruption of Kv3.4 expression and/or channel function may also slow the progression of, or even effect a cure of, Parkinson's disease and other neurological diseases and conditions. Although the invention is not limited to any particular hypothesis, the contemplated cure is predicated upon the observation that high frequency bursts result in the release of glutamate. The released glutamate was originally hypothesized to result in the death of neurons releasing dopamine. Disruption of Kv3.4 expression and/or channel function is contemplated to result in a concomitant diminution of STN mediated excitotoxic loading of dopaminergic neurons with synaptically released glutamate. In this way, the progression of the disease may be slowed or even halted.

Lastly, because the expression of Kv3.4 subunits is limited to a few cell populations outside the GP/STN axis, it is an excellent target for gene therapy. Infection of neighboring neurons should be of no consequence, since they don't express the targeted mRNA.

The present invention thus provides methods to ameliorate the pathophysiology of Parkinson's disease and its symptoms by delivery of genetic constructs that either diminish Kv3.4 expression or produce a Kv3.4 selective toxin, such as BDS-1, to neurons of the subthalamic nucleus or globus pallidus. These methods can be used as a therapy for Parkinson's disease patients, for example, at middle and late stages as an alternative to conventional therapies.

The following sections provide a description of some illustrative embodiments. These methods also find use in treating diseases for which the underlying pathophysiology is due to abnormal high frequency neuronal spiking, such as epilepsy.

I. Discovery that FS Neurons Kv3 Channels Possess Kv4.3a Subunit

Since the time of Hodgkin and Huxley, delayed rectifier currents have been known to be primary determinants of spike repolarization in neurons[1,2]. Recently, it has become clear that these currents are heterogeneous with properties tailored to the signaling and computational needs of particular neuronal classes. One group of neurons that has drawn a great deal of attention in this regard is the 'fast-spiking' (FS) class. These neurons can discharge at high rates for long periods with little spike frequency adaptation or attenuation in spike height. This property of FS neurons is attributable in large measure to their expression of fast delayed rectifier channels, which are channels that activate and deactivate very quickly[3].

At present, only Kv3 family potassium channels produce currents similar to those seen in neurons that spike at high rates[3,4]. There are four members of this family; two of them, Kv3.1 and Kv3.2, produce currents in heterologous expression systems resembling neuronal fast delayed rectifier currents. Both channels activate only at depolarized membrane potentials and have rapid activation and deactivation kinetics. Both are very sensitive to tetraethylammonium and 4-aminopyridine, as are fast delayed rectifier currents in neurons[5,6]. The discovery that Kv3.1 and/or Kv3.2 genes are expressed in FS neurons prompted early suggestions that Kv3 channels were responsible for fast delayed rectifier currents[7-9]. Subsequent studies, ranging from modeling to electrophysiological analysis of knockout animals, unambiguously support the conclusion that FS neurons depend upon K$^+$ channels containing Kv3.1 or Kv3.2 subunits.

However, there is a major problem with this story. In FS neurons, the fast delayed rectifier currents begin to activate near −30 mV with half-activation voltages between −18 and −7 mV[10,11]. In heterologous expression systems, Kv3.1/3.2 channel activation voltage dependence is much more depolarized with half-activation voltages well above 0 mV[12]. This is a critical difference. With the voltage dependence and activation kinetics seen in heterologous systems, only a small fraction of Kv3.1/2 channels will open during spike, making them very inefficient mediators of fast repolarization. Theoretical studies suggest there are two ways to deal with the problem. One strategy is to increase Kv3 current density to levels not seen in neurons[13]. The other strategy is to shift the voltage dependence of the Kv3 current toward more negative potentials, increasing the efficiency of the channels in spike repolarization as seen in neurons[3].

If Kv3 channels are responsible for delayed rectifier currents in FS neurons, then how can the differences in gating between native and heterologous channels be explained? Previous studies have shown that the FS phenotype is dependent upon the expression of a fast delayed rectifier current[3]. These currents activate rapidly during the up-stroke of the spike, resulting in rapid repolarization of the membrane. The narrow spikes characteristic of FS neurons minimize Na$^+$ channel inactivation, keeping the somatic and initial segment membrane responsive. Upon repolarization, these channels deactivate quickly, removing any impediment to subsequent depolarizing influences. Together, these features enable neurons to sustain spiking at high frequencies.

Many previous reports support the proposition that the fast delayed rectifier channel underlying FS behavior incorporates Kv3.1 and/or Kv3.2 subunits[3]. But, the view that these channels are Kv3.1/Kv3.2 homomers or heteromers of just these subunits is difficult to support. Although their gating kinetics are rapid, both Kv3.1 and Kv3.2 channels activate at significantly more depolarized potentials (~20 mV) than do native, fast delayed rectifier channels. This difference is critical. With the properties seen in heterologous systems, only a small fraction of Kv3.1/2 channels will open during spike, making them very inefficient mediators of fast repolarization.

During the development of the present invention, it was discovered that the repolarizing efficiency of Kv3 channels is increased by the incorporation of another subunit into the channel complex, the Kv3.4a subunit. Several lines of evidence, as described in more details in the Examples, support this conclusion. First, single cell RT-PCR profiling found co-expression of Kv3.4a and Kv3.1 mRNA in FS neurons from the globus pallidus, subthalamic nucleus, inferior colliculus and hippocampus. On the other hand, Kv3.4 mRNA was not found in regular spiking neurons from the hippocampus, striatum or basal forebrain. Second, co-immunoprecipitation experiments showed that Kv3.4 and Kv3.1 subunits are co-assembled in brain membranes and in HEK293 cells co-expressing Kv3.4a and Kv3.1b subunits. Co-expression of these subunits resulted in HEK293 cells yielded distinctive single channel currents and their macroscopic currents resembled those of Kv3 channels in FS neurons. Third, BDS-I, a Kv3.4 selective toxin, efficiently blocked TEA-sensitive, Kv3 channel currents in FS neurons. Together, these three observations show that Kv3 channels in many FS neurons contain Kv3.4 subunits.

Not only do Kv3.4a and Kv3.1 subunits co-assemble, but their association is sufficient to produce channels that strongly resemble Kv3 channels in neurons. Co-expression of Kv3.4a and Kv3.1b transcripts in HEK293 cells yielded currents with a sensitivity to BDS-I and TEA like that of native Kv3 channels. Moreover, these heterologously expressed, heteromeric channels had activation properties that were nearly identical to those of native channels and were efficiently activated by a spike waveform, in contrast to Kv3.1b homomeric channels. Kv3.1b/Kv3.4a heteromeric channels also had a rapidly inactivating component (~40 msec) at depolarized potentials, much like native Kv3 channels and unlike Kv3.1b homomeric channels. Inclusion of the Kv3.4a splice variant was essential to mimic native channels, as heteromers containing Kv3.4b or Kv3.4c subunits activated at potentials similar to those reported for Kv3.1 homomeric channels. On the face of it, this seems at odds with previous studies of Kv3.4a channels expressed in *Xenopus oocytes*, where they activated at more depolarized membrane potentials[16]. However, the half-activation voltage of Kv3.4a channels in these studies was 10-20 mV more negative than of Kv3.1/3.2 channels in the same preparation (as found here), suggesting that post-translational processing in mammalian cells shifts the voltage dependence of all Kv3 channels.

The small deviations in the inactivation and activation kinetics of the Kv3.4a/Kv3.1b channels in HEK293 cells from those in FS neurons may be attributable to differences in subunit stoichiometry. Both biophysical parameters were biased toward those of Kv3.4a channels in the studies described in the Examples, indicating that this subunit may have been expressed at relatively high levels. The differences also may be due to inclusion of Kv3.4c subunits in channels from FS neurons. The mRNA for this splice variant was found in all tested FS neurons, along with that of Kv3.4a. By varying the mix of Kv3.4a, Kv3.4c and Kv3.1 (or Kv3.2) subunits, it may be possible to 'tune' the properties of fast delayed rectifier channels to the particular needs of a neuronal class. The strategy of forming heteromeric channels to tune gating properties appears to be a common one used in the construction of K$^+$ channels in excitable cells[20-23].

Although the inclusion of Kv3.4a subunits in Kv3.1 channels increases their efficiency in spike repolarization in some FS neurons, other mechanisms could serve a similar end. It is clear from the immunoprecipitation experiments described in the Examples that much of the Kv3.1b protein in the brain is not associated with Kv3.4 protein. Moreover, in some brain regions, FS neurons are found but Kv3.4 mRNA appears to be absent. One such area is the medial nucleus of the trapezoid body (MNTB). In FS MNTB neurons, the voltage dependence of Kv3 channels is shifted toward more negative membrane potentials by dephosphorylation of the channel or a closely related protein[24]. Kv3.1 channels expressed in CHO cells are constitutively phosphorylated by casein kinase II and affected by dephosphorylation in much the same way[24]. Kinetically slower, Kv2.1 delayed rectifier channels also are phosphorylated early in their biosynthesis with a similar consequence for gating[25]. Could differential phosphorylation provide an alternative mechanism for regulating the gating of Kv3 channels? Perhaps, but phosphorylated MNTB Kv3 channels activate in a voltage range that is similar to that of the neuronal Kv3 channels studied here, which is significantly more negative than heterologously expressed Kv3.1 channels[24]. Another possibility is that an as-yet-unidentified accessory subunit is capable of modifying Kv3 channel gating in FS MNTB neurons, in much the same way as incorporation of the Kv3.4a subunit does in the neurons studies here[26].

An important feature of voltage gated K$^+$ channels is that the pore-forming region can be heteromeric, being composed of four independent subunits. The ability of Kv3.4a subunits to modify the gating of Kv3.1b channels illustrates how this capacity can be used to 'tune' properties to particular functional needs. By varying the stoichiometry of Kv3.4a and Kv3.4c subunits in the channel complex, a range of gating behaviors may be possible, allowing for a range of FS behaviors.

It is contemplated that variations on this theme underlies alterations in spiking behavior in pathophysiological states like Parkinson's disease and epilepsy.

II. Methods to Decrease Pathophysiological High Frequency Neuronal Bursting

In some embodiments, the present invention is directed to a strategy to treat Parkinson's disease and other neurological diseases and conditions, which is to selectively suppress the aberrant discharge behavior in the small population of neurons involved in the disease, without affecting the function of other nearby cells.

The present invention thus provides methods to ameliorate the pathophysiology of Parkinson's disease other neurological diseases and conditions and their symptoms by delivery of genetic constructs that either diminish Kv3.4 expression or produce a Kv3.4 selective toxin, such as BDS-1, to neurons of the subthalamic nucleus or globus pallidus. These methods can be used as a therapy for Parkinson's disease patients at middle and late stages as an alternative to conventional therapies.

A. Diminish Kv3.4 Expression

In some embodiments, the present inventions provides a method of manipulating neuronal ion channels, comprising transfecting a fast-spiking neuronal cell with a vector encoding an siRNA directed against an RNA encoding a Kv3.4 protein and capable of expression in the cell, wherein expression of the Kv3.4 protein is decreased.

Transfected Cells

The present invention also provides cells transfected by expression cassettes encoding an siRNA target to Kv3.4 mRNA, or by a vector (e.g., lentiviral vector) comprising an expression cassettes encoding an siRNA target to Kv3.4 mRNA. In some embodiments of the present invention, the host cell is a fast-spiking neuronal cell.

The cells are transfected transiently or stably; the cells are also transfected with an expression cassette of the present invention, or they are transfected with an expression vector of the present invention. The cells are cultured mammalian cells, preferably human cells, or they are tissue, organ, or organismal cells.

In some embodiments, the neuronal cell is in vitro or ex vivo; in other embodiments, the neuronal cell is in vivo. In particular embodiments, the neuronal cell is a globus pallidus neuron, a hippocampal interneuron, or a subthalamic neuron; in even more particular embodiments, the cell is a parvalbumin-expressing GABAergic, globus pallidus neuron, a parvalbumin-expressing GABAergic CA1 hippocampal interneuron, or a glutamatergic subthalamic neuron.

siRNA

The sequence for Kv3.4a is in Gene Bank under accession number X62841 (SEQ ID NO:6; gtgcgcttct ctgtctttct gggt-tgggg gggggcgtgtc cccggcccgg agcatccttg tgcttgcctc aacct-tctga gaccccggac cccttggatt gagtcctcga ccctggtctt cacctcctgc ctcccctagg ttcttcctgc caaatcccaa ccacctgtgc accacaaaaa gccaactctt cctgctccga gccccgggggg ggtgggggtgg ggggggaggca gggggcagagc cactctgcag aaggggccgc caccacctcc tgcctcctcc tcctcacca cctcctcctc cttctcgtct cctccccctc cccgttctga cgctgc-ctcc ttgggaaggg tgtttggagg gcagcggccg ccccaagccg gagc-cccgca gcgcttctta tgatcagctc ggtgtgtgtc tcctcctacc gcgggcg-caa gtcggggaac aagcctccgt ccaaacatg tctgaaggag gagatggcca agggcgaggc gtcggagaag atcatcatca acgtgggcgg cacgcgacat gagacctacac gcagcaccct gcgcaccctca ccgggcaccc gccttgcctg gctggcggat cccgacgggcg ggggtcggcc agagtcggat ggcggcggtg ggcggcggtg caggcagcag cggcagcagc ggcggcggcg ggggctgtga gttcttcttt gatcggcacc cgggtgtttt tgcctatgtg ctcaactact accg-cacggg caagctgcat tgccccgcag acgtctgtgg gcctctcttt gaggaa-gagc tcactttctg gggtatcgat gagacagatg tggaaccctg ctgctggatg acctaccggc agcaccgcga tgctgaagag gcactggaca tcttcgagag cccggacggg ggcggggggtg gcgcagggcc cggcgacgag gctg-gagacg atgagcggga gttggccttg cagcgcctgg gcccccatga aggag-gctct ggccctggtg ctgggtccgg gggttgccgt ggctggcagc cccgxit-gtg ggcgctcttc gaggacccgt actcatcccg ggcggccagg gtggtagcct ttgcctctct cttcttcatc ttggtctcca ttaccaccaccct ctgcctggag acccac-gagg ccttcaacat tgaccgaaat gtgacggaga tccaccgggt agggaatatc accagcgtgc gcttccggcg ggaggtagaa acagaaccca ttcttaccta catcgagggc gtgtgcgtga tgtggttcac tctagagttc ctggttcgca ttgtgt-gctg ccctgatacg ttggacttg tcaagaacct gctcaacatc atcgactttg tggccatctt gccctttac ctggaggtgg gattgagtgg cctgtcatcc aag-gcagctc gagatgtact gggtttcctg cgtgtggtgc gctttgtacg catcct-gcgg atcttcaagc tcacacgcca cttgtgggg ctgcgtgtgc tcggccacac actccgggcc agcaccaacg agttcctgct gcttatcatc ttcctggccc tgggt-gtgct catctttgcc accatgatct attatgctga gcgaatcggg gccaggccat ctgacccacg gggcaatgac cacaccgact tcaagaacat cccaatcggt ttctggtggg ctgtggtcac catgacaacg cttggctatg gggacatgta tcctaagaca tggtcaggaa tgctggtggg tgcgctgtgt gcactggctg gtgt-gctaac cattgccatg cctgtgcctg tcatcgtcaa taactttggt atgtactact ccctggctat ggccaagcag aagcttccca agaaacgaaa gaagcatgta ccacggccac cccagcttga gtcacccatt tactgcaagt ctgaggagac ttcaccccgg gacagcacct acagtgacac cagcccccct gcccggggaag agggtatggt cgagaggaaa cgagcagact ccaagcagaa tggtgacgct aatgcggtgc tgtccgatga ggagggagct ggcctcaccc agcccctggc ctcggccccc acccctgaag agcgtcgagc cctgagcgc tcaggcacac gggacagaaa caagaaggca gctgcctgct tcctgctcag tgctggggac tat-gcctgtg ctgatggcag tgtccagaaa gaaggcagtg ttgagccgaa agcgt-gcgtc ccagtgtctc acacctgtgc tctttaaaca cagagacctg ccaagacgcc ctctcgtcca actatgccca tgctgaagtc ctcaccctct cttagagcgg cac-caacgtg agaaagacag acagacagaa agccagaggc ttaggaaaac tctg-gaaccc aggcacgaat cttttgctgg gaaagatatc cttgtttgca caagactggt ggaaaaatct cccatgcaac tctcagggcc cagagccatc tgggtcgat actctgttct actgtacatt gaagagacat atatgcacat atagtatcta tat-tcataca tactatatac tcttgtgtgt agtgcacgtg ctactggtgg tctgtcttca tcgttaggct atgtctccca agtcctctgc ccaccctgtt tccccacccc ctcttc-cttc atggattgtt tcttctgacc atgtttttgg agtgtcccag gagaggtata cctgggacct gccccctccag ctgggtggtc ccaggctgct ctcacttggg ggt-gtcccct gccagcaggt ggcctgctga agtcagttga aggcacgatt gccct-tctgg ggtcactgct tcactagc). The sequence for Kv3.4c is identical to the Kv3.4a sequence except that 62 bp (position 2222-2283) of Kv3.4a are absent in Kv3.4c. As a result of this alternative splicing, the first 608 amino acids of both variants are identical, but the last 17 (for variant a) and 19 (for variant c) amino acids are completely different. Both variants are described by Rudy and colleagues in Veaga-Saenz de Miera E. et al. (1993) Shaw-related K channels in mammals. in Handbook of Membrane Channels: Molecular and Cellular Physiology. (Peracchia C, ed. Academic Press, Orlando) pp 41-78.

siRNAs are involved in RNA interference, where one strand of a duplex (the antisense strand) is complementary to a target gene RNA. The target of the siRNA is the 62 bp sequence absent in the Kv3.4c variant, or the sequences from position 2222-2283, are targeted by the siRNA.

In some embodiments of the present invention, an siRNA targeted to Kv3.4 mRNA comprises a double stranded RNA of about 18 to 25 base pairs long (ds siRNA); in other embodiments, the double strand is joined at one end by a loop of single stranded RNA (hairpin siRNA). A hairpin siRNA comprises a double-stranded region, where most but not necessarily all of the bases in the duplex region are base-paired, and where the two strands of the duplex are connected by a third strand; the duplex region comprises a sequence complementary to a target RNA. One strand of the duplex in hairpin siRNA is complementary to a target RNA; thus, it is an antisense sequence to the target RNA, whereas the opposite paired strand of the duplex siRNA is a sense sequence of (or the same sequence as) the target RNA. Either strand of the hairpin siRNA may be the antisense strand, as the order of the sense and antisense strands within a hairpin siRNA does not alter its inhibitory ability. Hairpin siRNA can be prepared as a single strand, which is contemplated to fold back into a hairpin structure. Different hairpin embodiments are contemplated.

In other embodiments, an siRNA targeted to Kv3.4 mRNA may comprise any one or more of the following: at least one mismatch in one of the strands of the duplex; a destination signal; additional sequences which confer additional structural stability; or additional sequences which result in post-transcriptional modifications.

In yet other embodiments, the two strands of the double-stranded region of the siRNA are expressed separately by two different expression cassettes, and then brought together to form a duplex in the cell.

In any of the siRNAs above, the sequence of the siRNA transcript is specific to the target Kv3.4 mRNA; such specificity is usually achieved by a double-stranded region of about 19 nucleotide pairs, although this region may be from about 18 to about 29 nucleotides long. It has also been observed that the siRNA transcript generally must have 100% homology with the target gene, meaning that the transcript must be completely homologous to a segment or region of the RNA of the target gene.

Techniques for preparing, administering, and expressing siRNAs in vitro, ex vivo, and in vivo are well known; such techniques have been reported, for example, in Ramaswamy, G, and Slack, F J (2002) Chem Biol 9(10): 1053-1055; Xia, H et al. (2002) Nat Biotechnol 20(10): 1006-1010; Lewis, D L et al. (2002) Nat Genet 32(1): 107-108; Yu, J Y et al. (2002) Proc Natl Acad Sci USA 99(9): 6047-6052; and Paul, C P et al. (2002) Nat Biotechnol 20(5): 505-508; which are all hereby incorporated by reference.

Expression Cassette siRNAs targeted to Kv3.4 may be synthesized chemically; chemical synthesis can be achieved by any method known or discovered in the art. Alternatively, siRNAs targeted to Kv3.4 may be synthesized by transcription. In some embodiments, transcription is in vitro, as from a DNA template and bacteriophage RNA polymerase promoter; in other embodiments, synthesis is in vivo, as from a gene and a promoter, as described further below. Separate-stranded duplex siRNA (ds siRNA), where the two strands are synthesized separately and annealed, can also be synthesized chemically by any method known or discovered in the art. Alternatively, ds siRNA are synthesized by transcription. In some embodiments, the two strands of the double-stranded region of a siRNA are expressed separately by two different expression cassettes, either in vitro (e.g., in a transcription system) or in vivo in a host cell, and then brought together to form a duplex.

Thus, in some embodiments, the siRNA targeted to Kv3.4 can be applied directly to fast-spiking neurons; in these embodiments, the siRNA may comprise a ds siRNA, or a hairpin siRNA. In alternative embodiments, the siRNA is expressed in situ from an expression cassette comprising a promoter and a gene which encodes an siRNA. In some embodiments, the transcribed siRNA forms a double stranded RNA of about 18 to 29 base pairs long. In other embodiments, the transcribed siRNA forms a double stranded RNA of about 18 to 29 base pairs long, and further comprises a loop which joins the two strands at one end, as described in any of the embodiments above.

A single strand of siRNA can be initially transcribed as a single RNA strand, which is contemplated to then fold into a hairpin structure. A promoter of an expression cassette may be constitutive or inducible; the promoter is preferably tissue or organ specific. Preferably, the promoter is positioned 5' to the transcribed region; in one embodiment, the promoter is a U6 gene promoter. Other promoters are also contemplated; such promoters include other polymerase III promoters and microRNA promoters, suitably modified as necessary. Other promoters include but are not limited to a wide range of neuronal and glia specific promoters. Such promoters include currently known promoters, as well as promoters discovered, which result in expression of the vector in the neuronal cells.

Preferably, the expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

Vectors

In other embodiments, the siRNA is administered to fast-spiking neuronal cells in a vector comprising at least one expression cassette; the vectors may further or instead comprise marker genes, reporter genes, selection genes, or genes of interest, such as experimental genes. A vector may also include sites for stable integration into a host cell genome.

In some embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed and viable in the host; these criteria are sufficient for transient transfection. For stable transfection, the vector is also replicable in the host.

Large numbers of suitable vectors are known to those of skill in the art, and are commercially available. In some preferred embodiments of the present invention, mammalian expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements. In some embodiments, vectors express either a single strand of ds siRNA, or a hairpin siRNA. In other embodiments, for vectors encoding a single strand of a ds siRNA, formation of ds siRNA in a cell requires co-transfection of a single cell with two vectors, each encoding one of the two strands; upon expression of the vectors, the two strands combine to form ds siRNA. In yet other embodiments, a single vector expresses both strands of a ds siRNA; in this vector, each coding sequence for a single strand of the ds siRNA may be under control of its own promoter (for example, a U6 promoter), or the two coding sequences may be encoded by a single sequence which has a cleavage site between the two strands and which is under control of a single promoter.

In certain embodiments of the present invention, a gene sequence in the expression vector which is not part of an expression cassette encoding siRNA is operatively linked to an appropriate expression control sequence(s) (promoter) to direct mRNA synthesis. Promoters useful in the present invention include, but are not limited to, the cytomegalovirus (CMV) immediate early, herpes simplex virus (HSV) thymidine kinase, and mouse metallothionein-I promoters and other promoters known to control expression of gene in mammalian cells or their viruses. In other embodiments of the present invention, recombinant expression vectors include origins of replication and selectable markers permitting transformation of the host cell (e.g., dihydrofolate reductase or neomycin resistance for eukaryotic cell culture).

In some embodiments of the present invention, transcription of the DNA encoding a gene is increased by inserting an enhancer sequence into the vector. Enhancers are cis-acting elements of DNA, usually about from 10 to 300 bp that act on a promoter to increase its transcription. Enhancers useful in the present invention include, but are not limited to, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

Exemplary vectors include, but are not limited to, the following eukaryotic vectors: pWLNEO, pSV2CAT, pOG44, PXT1, pSG (Stratagene) pSVK3, pBPV, pMSG, pSVL (Pharmacia). Particularly preferred plasmids are the Adenovirus vector (AAV; pCWRSV, Chatterjee et al. (1992) Science 258: 1485), a retroviral vector derived from MoMuLV (pG1Na, Zhou et al. (1994) Gene 149: 3-39), and pTZ18U (BioRad, Hercules, Calif., USA). Exemplary lentiviral vector systems include pLentilox3.7 plasmid with packaging plasmids VSVG, RSV-REV and pMDL g/p RRE. Exemplary vectors include but are not limited to retrovirus based vectors with neuron specific promoter are used for expression of siRNAs, with a wide range of neuronal and glia specific promoters. Such promoters include currently known promoters, as well as promoters discovered, which result in expression of the vector in the neuronal cells.

Methods to Transfect Cells

The present invention also provides methods of transfecting a neuronal cell with an expression cassette or with a vector as described above, which encodes an siRNA targeted to Kv3.4. The present invention also provides methods of expressing siRNA in a neuronal cell by transfecting the cell with an expression cassette or with a vector as described above. The present invention also provides methods of silencing a Kv3.4 expression in a neuronal cell by transfecting the cell with an expression cassette or with a vector as described above, where the siRNA encoded by the expression cassette targets Kv3.4 mRNA. In these methods, the cell is transfected transiently or stably, and the cell is a cultured neuronal cell, preferably a human cell, or it is a tissue, organ, or organismal neuronal cell. Furthermore, in the methods the siRNA encoded by the expression cassette or vector upon transcription forms a double stranded RNA of about 18 to 25 base pairs long. In other words, the siRNA is a ds siRNA or a hairpin siRNA.

1. Transfection

In the present invention, cells to be transfected in vitro or ex vivo are typically cultured prior to transfection according to methods which are well known in the art, as for example by the preferred methods as defined by the American Tissue Culture Collection or as described (for example, Morton, H. J., In Vitro 9: 468-469 (1974). When cells to be transfected are in vivo, as in a tissue, organ, or organism, the cells are transfected under conditions appropriate for the specific organ or tissue in vivo; preferably, transfection occurs passively.

Expression cassettes or vectors comprising at least one expression cassette can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

In some embodiments, various methods are used to enhance transfection of the cells. These methods include but are not limited to osmotic shock, temperature shock, and electroporation, and pressure treatment. In pressure treatment, plated cells are placed in a chamber under a piston, and subjected to increased atmospheric pressures (for example, as described in Mann et al., *Proc Natl Acad Sci USA* 96: 6411-6 (1999)). Electroporation of the cells in situ following plating may be used to increase transfection efficiency. Plate electrodes are available from BTX/Genetronics for this purpose.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce an expression or vector in vivo as a naked DNA, either as an expression cassette or as a vector. Methods for formulating and administering naked DNA to mammalian muscle tissue are disclosed in U.S. Pat. Nos. 5,580,859 and 5,589,466, both of which are herein incorporated by reference.

Stable transfection typically requires the presence of a selectable marker in the vector used for transfection. Transfected cells are then subjected to a selection procedure; typically, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

Although the compositions and methods of the present invention are applicable to situations in which short-term effects of siRNA are to be examined in vitro, such effects can also be observed by adding synthetic siRNA, as has been reported (as, for example, by Elbashir et al. (2001) *Nature* 411: 494-498). However, in situations in which long-term effects of siRNA are to be examined, it is preferable and in fact necessary to utilize intracellular expression of siRNA. Moreover, it is also necessary to use intracellular expression of siRNA for in vivo effects, as in gene therapy and research applications.

2. Detection of Gene Silencing

The effectiveness of siRNA in a cell can be determined by measuring the degree of gene silencing. Gene silencing can be monitored by a number of means. A "silenced" gene is evidenced by the disappearance of the RNA, or less directly by the disappearance of a protein translated from the RNA.

Detection of the loss of RNA is a more direct measure of gene silencing than is detection of protein disappearance, as it avoids possible artifacts that may be the results of downstream processing. RNA can be detected by Northern blot analysis, ribonuclease protection assays, or RT-PCR. However, measurement of RNA is cumbersome. Therefore, preferred assays measure the presence of a gene protein product.

Proteins can be assayed indirectly by detecting endogenous characteristics, such as by functional activity or directly by using antibody-based assays. For example, for transfected neuronal cells, effective silencing of Kv3.4 expression may be monitored by measuring the ability of the cell to exhibit pathological high frequency spiking; such cells may be in vitro or in vivo. Exemplary methods for measuring the spiking ability of the neurons, as well as characteristics and properties of transfected neurons, are described in the Examples.

B. Administer a Kv3.4 Selective Toxin

In other embodiments, the present invention provides a method of manipulating neuronal ion channels, comprising transfecting a fast-spiking neuronal cell with a vector encoding a gene encoding a toxin directed against Kv3.4 subunits and capable of expression in the cell, under conditions such that the toxin is expressed. Preferably, the capability of the neuron to exhibit pathophysiological fast-spiking is inhibited, wherein it's ability to exhibit normal physiological fast-spiking is relatively unaffected.

In some embodiments, the cell expresses a Kv3.4a subunit. In further embodiments, the neuronal cell is in vitro or ex vivo; in other embodiments, the neuronal cell is in vivo. In particular embodiments, the neuronal cell is a globus pallidus neuron, a hippocampal interneuron, or a subthalamic neuron; in even more particular embodiments, the cell is a parvalbumin-expressing GABAergic, globus pallidus neuron, a parvalbumin-expressing GABAergic CA1 hippocampal interneuron, or a glutamatergic subthalamic neuron.

In other embodiments, the present invention provides a method of manipulating neuronal ion channels, comprising transfecting a cell which can be transplanted into the vicinity of a fast-spiking neuronal cell with a vector encoding a gene encoding a toxin directed against Kv3.4 subunits and capable of expression in the cell, under conditions such that the toxin is expressed and can taken up by a fast-spiking neuronal cell. In some embodiments, BDS-I is secreted from the transfected cell. Preferably, the capability of the neuron to exhibit pathophysiological fast-spiking is inhibited, wherein it's ability to exhibit normal physiological fast-spiking is relatively unaffected. In some embodiments, the transfected cell is transplanted in the vicinity of a fast-spiking neuronal cell. In further embodiments, the neuronal cell is in vitro or ex vivo; in other embodiments, the neuronal cell is in vivo. In particular embodiments, the neuronal cell is a globus pallidus neuron, a hippocampal interneuron, or a subthalamic neuron; in even more particular embodiments, the cell is a parvalbumin-expressing GABAergic, globus pallidus neuron, a parvalbumin-expressing GABAergic CA1 hippocampal interneuron, or a glutamatergic subthalamic neuron.

In some embodiments, the encoded toxin is BDS-1. The amino acid sequence for the toxin BDS-1 is described in Diochot S. et al. (1998). Sea anemone peptides with a specific blocking activity against the fast inactivating potassium channel Kv3.4. J Biol Chem 273 (12): 6744-6749, 1998. BDS-I is also described in a patent application (Beress L. et al. (Jan. 17, 1985) Federal Republic of Germany Patent DE 33 24 689 A1).

Vectors and methods of transfecting cells are described above. Retrovirus based vectors with neuron specific promoter are used for expression of BDS-1 in the neuronal cells. A wide range of neuronal and glia specific promoters can be used; such promoters include those currently known and those discovered, which control expression of a coding sequence for BDS-I in neuronal cells. Assays for measuring the effects of the toxin on fast-spiking neurons, and in particular on the Kv3.4 channel, are described above and in the Examples.

In other embodiments, the encoded toxin is analyzed as described below. Effective toxins are identified by screening methods as described below.

In yet other embodiments, the present invention provides a method of manipulating neuronal ion channels, comprising administering to a fast-spiking neuronal cell a compound directed against Kv3.4 subunits; in particular embodiments, the capability of the neuron to exhibit pathophysiological fast-spiking is inhibited, wherein it's ability to exhibit normal physiological fast-spiking is relatively unaffected. Effective compounds are identified by screening methods, as described below.

In some embodiments, the compound is able to cross the blood brain barrier. Methods to deliver compounds directed against Kv3.4 channels include the ability to "cross" the blood-brain barrier that is formed by brain capillary endothelial cells. Since the endothelial cells are connected to each other by tight junctions and lack pores and/or fenestrations, compounds must cross the membranes of the cells to enter the brain from the bloodstream. Appropriate delivery methods include but are not limited to: continuous infusion of the compound(s) into the central spinal fluid, such as by programmed infusion pumps, in some cases computer controlled; systemic administration of inactive prodrugs which are activated at the site of fast-spiking neurons by locally released compounds, as for example a compound linked to a sugar or lipid or protein moiety, which moiety is cleaved off by an endogenous hydrolytic enzyme such as a lipase or protease; administration of liposomes and nanoparticles, engineered micro-reservoirs of a drug, with attached antibodies or receptor-specific binding agents designed to target the particles to a specific region of the body, which could deliver a high concentration of a compound to fast-spiking neurons; linking a compound to an iron transferrin or biological toxin that can cross the blood-brain barrier; utilizing cell transplants that generate neurotransmitters and neuromodulators, which provide renewable endogenous drug delivery; and gene therapy which use adenovirus, adeno-associated virus, herpesvirus or other delivery vectors to induce brain cells to produce local modulatory substances.

Some of these methods include modifying compounds directed against Kv3.4 channels such that they cross the blood-brain barrier by a transporter. Transporters that are involved in drug transfer across the BBB and have been identified and characterized. Most of these transporters function in the direction of influx from blood to brain, and include transporters for amino acids, monocarboxylic acids, organic cations, hexoses, nucleosides, and peptides. Thus, modified compounds directed against Kv3.4 channels comprise a moiety recognized and transported by a transporter; the moiety either does not affect the activity of the compound against Kv3.4, or it is cleaved off by an internal enzyme. For example, cellular delivery systems based on conjugates of streptavidin and the OX26 monoclonal antibody directed to the transferrin receptor may be employed as a carrier for the transport of mono-biotinylated peptides, antisense oligonucleotides or peptide encoding nucleotides (Boado RJ et al. (1998) J Pharm Sci 87(11):1308-15), where such compounds are directed against Kv3.4 ion channels.

C. Therapeutic Compositions

The present invention also provides compositions comprising at least one expression cassette encoding an siRNA which targets Kv3.4, as described above.

In other embodiments, the present invention provides a central nervous system cell transfected with a vector comprising a gene encoding a toxin directed against Kv3.4 subunits and capable of expression in the cell, as described above.

The present invention also includes pharmaceutical compositions and formulations that include the compounds directed against Kv3.4 of the present invention; exemplary compounds include siRNAs directed against Kv3.4 mRNA, antisense oligonucleotides, genes encoding toxins or compounds directed against Kv3.4, and toxins or compounds directed against Kv3.4. The pharmaceutical compositions of the present invention may be administered in a number of ways depending upon whether local or systemic treatment is desired and upon the area to be treated. Administration may be through cell transplantation, topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

For implantation of cells into the brain, stereotaxic methods may be used (See e.g., Leksell and Jernberg, Acta Neurochir. 52:1 [1980]; and Leksell et al., J. Neurosurg. 66:626 [1987]). Methods for transplanting cells to specific regions of the central nervous system are taught by U.S. Pat. No. 5,650,148, incorporated herein by reference. These neural transplantation or "grafting" methods involve transplantation of cells into the central nervous system or into the ventricular cavities or subdurally onto the surface of a host brain. Methods for transplanting various nerve tissues have been described in Neural Grafting in the Mammalian CNS, (Bjorklund and Stenveni, eds. [1985]); Das, Ch. 3 pp. 23-30; Freed Ch. 4, pp. 31-40; Stenevi et al., Ch. 5, pp. 41-50; Brundin et al., Ch. 6, pp. 51-60; David et al., Ch. 7, pp. 61-70; and Seiger, Ch. 8, pp. 71-77), herein incorporated by reference. In some grafting embodiments, the cell suspension is drawn up into a syringe and administered to anesthetized graft recipients. Multiple injections may be made using this procedure.

III. Methods for Screening Compounds that Specifically Interfere with Kv3.4a

The present invention also provides methods for screening compounds that specifically interfere with Kv3 channels that comprise a Kv3.4 subunit; such methods are contemplated to be applied to development of treatment without gene therapy.

It is contemplated that some compounds which specifically interfere with Kv3 channels which comprise a Kv3.4 subunit bind to the Kv3.4 subunit. Therefore, in some embodiments, the methods comprise initially screening for compounds which bind to a Kv3.4 subunit, preferably to the Kv3.4a subunit. Those compounds which bind to a Kv3.4 subunit are then screened for their ability to specifically interfere with Kv3 channel functioning, where the Kv3 channels comprise the Kv3.4a subunit. In other embodiments, the methods comprise screening for compounds for their ability to specifically interfere with Kv3 channel functioning, where the Kv3 channels comprise the Kv3.4a subunit.

In some embodiments, the present invention provides screening methods for identifying modulators, i.e., candidate or test compounds or agents (e.g., proteins, peptides, peptidomimetics, peptoids, small molecules or other drugs) which bind to Kv3.4 of the present invention, or have an inhibitory effect on, for example, Kv3.4 expression or Kv3 channel activity. Compounds thus identified can be used to modulate the activity of target gene products (e.g., Kv3.4a genes) either directly or indirectly in a therapeutic protocol, to elaborate the biological function of the target gene product, or to identify compounds that disrupt normal target gene interactions.

In some embodiments, the invention provides assays for screening candidate or test compounds that bind to Kv3.4.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckermann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carrell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In some embodiments, an assay is a cell-based assay in which a cell that expresses a Kv3.4 protein or biologically active portion thereof is contacted with a test compound, and the ability of the test compound to bind to Kv3.4 is determined In yet other embodiments, a cell-free assay is provided in which a Kv3.4 protein or biologically active portion thereof is contacted with a test compound and the ability of the test compound to bind to the Kv3.4 protein or biologically active portion thereof is evaluated. Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the Kv3.4 protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In some embodiments, Kv3.4 or the test substance is anchored onto a solid phase. The Kv3.4/test compound complexes anchored on the solid phase can be detected at the end of the reaction. Preferably, the Kv3.4 peptide can be anchored onto a solid surface, and the test compound, (which is not anchored), can be labeled, either directly or indirectly, with a detectable labels.

In some embodiments, the methods provide high throughput screening for compounds having suitable binding affinity to Kv3.4a peptides, such as are described in detail in WO 84/03564, incorporated herein by reference. Briefly, large numbers of different small peptide test compounds are synthesized on a solid substrate, such as plastic pins or some other surface. The peptide test compounds are then reacted with Kv3.4 peptides and washed. Bound Kv3.4 peptides are then detected by methods well known in the art.

Another technique uses Kv3.4 antibodies. Such antibodies capable of specifically binding to Kv3.4 peptides compete with a test compound for binding to Kv3.4. In this manner, the antibodies can be used to detect the presence of any peptide that shares one or more antigenic determinants of the Kv3.4 peptide.

The present invention also provides methods for identifying modulators of Kv3.4 expression. For example, a cell or cell free mixture is contacted with a candidate compound and the expression of Kv3.4 mRNA or protein evaluated relative to the level of expression of Kv3.4 mRNA or protein in the absence of the candidate compound. When expression of Kv3.4 mRNA or protein is less (i.e., statistically significantly less) in the presence of the candidate compound than in its absence, the candidate compound is identified as an inhibitor of Kv3.4 mRNA or protein expression. The level of Kv3.4 mRNA or protein expression can be determined by methods for detecting Kv3.4 mRNA or protein.

A modulating agent can be identified using a cell-based or a cell free assay, and the ability of the agent to modulate the expression of Kv3.4 protein can be confirmed in vivo, e.g., as described further below.

The present invention contemplates many other means of screening compounds for binding to a Kv3.4 protein or to modulating expression of Kv3.4 mRNA or protein. The examples provided above are presented merely to illustrate a range of techniques available. One of ordinary skill in the art will appreciate that many other screening methods can be used.

In some embodiments, the methods comprise contacting a cell expressing homomeric Kv3.4 channels with a test compound, and measuring the resulting currents. Compounds that interfere with Kv3 channels, and specifically with Kv3.4 subunits of Kv3 channels, slow the rising phase of the current, but lead to larger currents later in the step. Exemplary methods are provided in the Examples (and in particular, Examples 1 and 5). In some embodiments, the test compound is a compound that binds to Kv3.4 peptide, identified as described above.

In other embodiments, the methods of the present invention comprise contacting a fast-spiking cell expressing Kv3 channels with a test compound, and measuring the resulting spikes. Compounds that interfere with Kv3 channels, and specifically with Kv3.4 subunits of Kv3 channels, substantially broaden the spikes, and slow the rate of repetitive spiking evoked by sustained current injection in fast-spiking neurons. Exemplary methods are provided in the Examples (and in particular, Examples 1 and 5). In some embodiments, the test compound is a compound that binds to a Kv3.4 peptide, identified as described above.

Experimental

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); tetraethylammonium (TEA); polymerase chain reaction (PCR); reverse tail PCR (RT-PCR); single cell RT-PCR (scRT-PCR); polyacrylamide gel electrophoresis (PAGE); fast spiking (FS); blood depressing substance (BDS); globus pallidus (GP); subthalamic nucleus (STN).

EXAMPLE 1

Methods

This example describes the methods used in discovering the role of the subunit Kv3.4 in FS neurons.

Tissue preparation. Neurons from the GP, subthalamic nucleus, inferior colliculus and CA1 area of hippocampus from young adult rats were acutely dissociated, using procedures similar to those we have described previously[27]. Hippocampal interneurons and GP were identified as CaMKII negative, GAD67 and parvalbumin positive neurons by single cell RT-PCR detection of corresponding mRNAs following physiology experiments (see below).

Electrophysiology. Whole-cell recordings used standard techniques[27,28]. The internal solution consisted of (in mM): 30-90 $K_2SO_4$, 0-60 N-methyl-D-glucamine, 2 $MgCl_2$, 40 HEPES, 5 EGTA, 12 phosphocreatine, 2 $Na_2ATP$, 0.2 $Na_3GTP$, and 0.1 leupeptin, pH 7.2 with $H_2SO_4$ (osmolarity 260-270 mOsm/l). The external solution consisted of (in mM): 140 Na-isethionate, 2 KCl, 4 $MgCl_2$, 10 HEPES, 12 glucose and 0.001 TTX, pH 7.35 with NaOH (osmolarity 295-305 mOsm/l). The internal solution for current clamp recordings consisted of (in mM) 110 potassium methylsulphate, 2 $MgCl_2$, 40 HEPES, 5 EGTA, 12 phosphocreatine, 2 $Na_2ATP$, 0.2 $Na_3GTP$, and 0.1 leupeptin, pH 7.2 with $H_2SO_4$ (osmolarity 260-270 mOsm/l). In the case of current clamp recordings, TTX was omitted from external solution. For the recordings in the presence of $Ca^{+2}$ ions EGTA was omitted from internal solution and 4 mM of $MgCl_2$ was substituted by 2 mM of $CaCl_2$ and 2 mM of $MgCl_2$. All drugs were obtained from Sigma (St. Louis, MN) except BDS-I that was obtained from Alomone Labs (Jerusalem, Israel). Solutions were applied by gravity fed sewer pipe system. Recordings were obtained with Axon Instruments 200 patch-clamp amplifier and controlled and monitored with a PC running pClamp software (version 7.0) (Axon Instruments Inc., Union City, Calif.). Electrode resistance was typically 1.5-2.2 MΩ in the bath. After seal rupture, series resistance (2-10 MΩ) was compensated (75-90%) and periodically monitored. In the case of application action potential waveform the cells were selected for relaxation times <0.3 msec. Potentials were not corrected for the liquid junction potential, which was estimated to be 1-2 mV. All averaged data presented as an average±standard error of the mean. All data fits were obtained using Igor Pro (WaveMetrics, Inc., OR) software by least square method. Activation data were fit with a Boltzmann equation of the form: $1/(1+\exp((V_h-V)/V_c))$, V stands for membrane potential. In the case of Kv3.4a current, an estimate of peak current was obtained by single exponential fit of decay phase extrapolated to the start of test pulse. In all other instances the voltage dependence of the currents was obtained from the amplitude of tail currents measured following 200 msec long voltage steps.

Single channel recordings were made from HEK293 cells using the cell-attached variation of the patch clamp technique. HEK293 cells were transfected with Kv3.1, or Kv3.4 or both Kv3.1 and Kv3.4 cDNA. The patch pipettes were pulled from 0.8 mm (i.d.) borosilicate glass capillary tubes with filament (G150F-4, Warner Instrument Corp, Hamden, Conn.) to the final resistance of 15 MΩ when filled with extracellular recording solution. The electrodes were coated with a semiconductor protective coating material R-6101 (Dow Corning Corporation, Midland, Mich.) and fire-polished. The signals were recorded using an Axopatch 200 amplifier and stored in a microcomputer via analog to digital converter. From a holding potential of -100 mV, patches were depolarized to potentials between 0 and +40 mV (700 ms). The resting membrane potential measured at the end of experiments was typically −40 mV. The temporal properties of single channel events were analyzed with pClamp8 software. The slope conductance was calculate from the single channel currents measured between 0 and +40 mV. Closed times less than 5 ms were considered to be part of a burst; the mean closed time within unambiguous bursts was 1.5 ms. Using this criterion, the probability that a gap or closing within a burst will be mis-identified as a between burst closing is less than 5%.

Single cell RT-PCR (scRT-PCR). Two types of scRT-PCR profiling were performed. To maximize mRNA yields, some neurons were aspirated without recording. Isolated neurons were patched in the cell-attached mode and lifted into a stream of control solution. Neurons were then aspirated into an electrode containing sterile water. In other experiments, neurons were briefly subjected to whole cell voltage clamp recordings prior to aspiration. In these cases, the electrode recording solution was made nominally RNase-free. RT procedure was performed using SUPERSCRIPT First-Strand Synthesis System (Invitrogen). Primers for PCR were described previously[19,29,30]. Heterologous expression. Kv3.4a and Kv3.4c cDNA was sub-cloned into pcDNA3 (Invitrogen). Kv3.1b cDNA clone was a gift from Dr. Bernardo Rudy. HEK293 cells were transfected using Effectene Transfection Reagent (QIAGEN). Cells were used for whole-cell recordings or harvested for membrane extraction 36-60 hr after transfection. In the case of co-transfection with Kv3.4a and Kv3.1b cDNA, single cell RT-PCR was used to confirm the presence of both mRNAs in the recorded cell. The presence of both inactivating and non-inactivating components of potassium current was an additional criterion for cell selection.

Immunoprecipitation. The crude membranes were solubilized in lysis buffer (1% Triton X-100, 150 mM NaCl, 1 mM EDTA, 10 mM Tris-HCl, pH 8.0) containing a protease inhibitor mixture[31]. Samples were incubated for 1 hr at 4C on a rotator, followed by addition of Anti-Kv3.1b or Anti-Kv3.4 antibodies (Alomone Labs) and further incubation for 1 hr. Then protein A-Sepharose was added. After 45 min incubation, protein A-sepharose was pelleted by centrifugation at 10,000×G for 30 sec and resulting pellets were washed 6 times with lysis buffer. The final pellets were re-suspended in reducing SDS sample buffer.

SDS-polyacrylamide gels and immunoblotting. Products of immunoprecipitation reactions were size fractionated on a 10% SDS-polyacrylamide gel. After electrophoretic transfer to nitrocellulose, the resulting blots were blocked in Blotto, incubated in Anti-Kv3.1b or Anti-Kv3.4 antibodies for 1 hr, and washed 4 times in TBS. Blots were then incubated in HRP-conjugated secondary antibody (PerkinElmer) and washed 4 times in TBS, followed by Chemiluminescence Reagent Plus (PerkinElmer).

EXAMPLE 2

Kv3.1 Homomeric Channels Differ from FS Delayed Rectifier Channels

Three types of neuron (identified by scRT-PCR) in which Kv3 channel currents are thought to be key regulators of repetitive activity were studied: parvalbumin-expressing GABAergic, globus pallidus neurons, parvalbumin-expressing, GABAergic CA1 hippocampal interneurons and glutamatergic subthalamic neurons[10,11,14]. All three types of neuron are capable of sustained high frequency (>100 Hz) discharge without significant accommodation and will be referred to as fast-spiking (FS). A key feature of Kv3 channel currents in these neurons is their activation during the upstroke of the spike, leading to rapid repolarization of the membrane potential and brief spikes. The ability to be activated efficiently during the upstroke of the spike depends upon the voltage at which channels begins to open and the rate at which they enter the open state.

In FS neurons, tetraethylammonium (TEA)-sensitive, Kv3 channels begin to activate just above spike threshold (ca. −30 mV). A spike waveform obtained from an FS neuron at the same temperature does an excellent job of activating these channels and evoking current. To quantify the relative repolarizing efficiency of native channels, the amplitude of the current evoked by the spike waveform was divided by the amplitude of the current evoked by a long step to the voltage reached by the peak of the action potential (+30 mV). On average, the repolarizing efficiency of fast, Kv3 delayed rectifier channels in FS neurons was 0.42±0.03 (n=6).

In contrast, homomeric Kv3.1b channels expressed in HEK293 cells yielded $K^+$ currents that activated at relatively depolarized membrane potentials. The same action potential waveform evoked little Kv3.1b current. On average, the efficiency of Kv3.1b current was 0.09±0.02 (n=4), which is about one-fourth that of Kv3 channel currents in FS neurons.

There were two obvious reasons for the greater efficiency of the neuronal channels. First, as mentioned, the Kv3 channels in FS neurons activated at significantly more negative membrane potentials than did homomeric Kv3.1b channels. The steady state half-activation voltage of Kv3 channels in FS neurons was around −15 mV, whereas it was near +7 mV for Kv3.1b channels—a 22 mV difference. Second, the negative shift in the voltage dependence of activation was paralleled by a shift in activation kinetics. At depolarized membrane potentials, the relationship between membrane voltage and activation time constant in FS neurons was shifted by about the same amount (18 mV) as the steady-state activation curves. This led to a significant acceleration in the opening of neuronal Kv3 channels during the up-stroke of the spike (between −20 and 30 mV).

EXAMPLE 3

FS Neurons Co-express Kv3.1 and Kv3.4a Subunits

In agreement with in situ hybridization work previously reported[8], prior scRT-PCR studies by the inventors had shown that GABAergic GP neurons expressed Kv3.1 mRNA and TEA-sensitive, fast delayed rectifier channels[11]. As a first step toward understanding the origin of the biophysical difference between these FS neuronal channels in situ and Kv3.1 homomeric channels expressed in HEK293 cells, scRT-PCR profiling of the FS neurons was expanded to include the other members of the Kv3 family, despite previous reports that Kv3.3 and Kv3.4. Kv3.3 mRNA was rarely detected in GP neurons.

But in contrast to previous reports, GABAergic GP neurons consistently expressed both Kv3.1 and Kv3.4 mRNAs. Kv3.4 mRNA was detected in 96% (45/47) of the GP sample. In fact, GP neurons co-expressed two of the three known Kv3.4 splice variants. These splice variants appeared as a small (c variant, 460 bp) and a large (a variant, 522 bp) amplicon in the scRT-PCR profiles. Sequencing verified their identity. Both Kv3.4 mRNAs were relatively abundant in these neurons, and could be reliably detected with as little as 10% of the total cellular cDNA.

To determine if this expression pattern was peculiar to GP FS neurons, other cell types were profiled. Surprisingly, Kv3.4 mRNA was reliably detected in all the FS neurons examined; subthalamic neurons (100%, 13/13), hippocampal parvalbumin GABAergic interneurons (100%, 8/8) and inferior collicular neurons (100%, 7/7) all expressed Kv3.4 mRNA. Moreover, in all of these cell types, Kv3.4 was abundant with detection requiring as little as 10% of the total cellular cDNA.

In contrast, Kv3.4 mRNA was not detected in neurons that did not display FS behavior. ScRT-PCR profiling of striatal cholinergic interneurons (n=27), of striatal medium spiny neurons (n=8), of basal forebrain cholinergic neurons (n=37) and of pyramidal neurons (from hippocampus) (n=10) failed to detect Kv3.4 mRNA, even with up to 50% of the total cellular cDNA as a template.

The co-expression of Kv3.4 and Kv3.1 mRNAs in FS neurons raised the possibility that they form heteromers, resulting in channels with altered properties. To determine whether these subunits co-assembled, attempts were made to immunoprecipitate Kv3.1 protein with an antibody to the Kv3.4 subunit. Kv3.1b protein was detected in brain membranes precipitated with Kv3.4 antibody but was absent when Kv3.4 antibody was pretreated with Kv3.4 peptide or if the antibody was omitted. Kv3.1b protein was not detected in brain membranes precipitated with Kv4.2 antibody. Stripping and re-probing the same western blot with Kv3.4 antibody confirmed the association of Kv3.1b and Kv3.4 protein in a significant fraction of channels, as Kv3.1b precipitates were labeled by Kv3.4 antibody. Kv3.4 and Kv3.1 subunits also co-assembled when expressed in HEK293 cells. Membrane protein precipitated with Kv3.4 antibodies from HEK293 cells co-transfected with Kv3.1b and Kv3.4a cDNA was recognized by the Kv3.1 probe. Conversely, Kv3.1 precipitates from these co-transfected cells were recognized by the Kv3.4 antibody. The antibodies did not cross-react, as transfection of HEK293 with a single subunit resulted in protein that was only recognized by the appropriate antibody not from cell expressing Kv3.1b. Taken together, these results show that FS neurons co-express Kv3.1 and Kv3.4 mRNA and that these channel subunits co-assemble.

EXAMPLE 4

Kv3.4a Shifts the Activation Voltage-dependence of Kv3 Channels

If a key feature of Kv3 channels in FS neurons depend solely upon co-assembly of Kv3.4 and Kv3.1 subunits, then expression of just these subunits in a heterologous system should yield $K^+$ currents like those found in FS neurons. To test this hypothesis, Kv3.1 and Kv3.4 subunits were cloned and expressed in HEK293 cells. Expression of Kv3.4a subunits in HEK293 cells yielded currents that activated rapidly and then inactivated, as described previously for Kv3.4 channels[3,15,16]. At 10 mV, the Kv3.4a currents decayed monoexponentially with a time constant of 20±5 msec (n=4). However, unlike previous descriptions, Kv3.4a channels activated at relatively hyperpolarized membrane potentials, having a steady-state half-activation voltage (−15 mV) near that found for Kv3 currents in FS neurons. This relatively hyperpolarized activation voltage-dependence was isoform specific, as the activation profile of Kv3.4c channels resembled that previously reported for Kv3.4b channels[3]. Homomeric Kv3.4a channels also had faster activation kinetics than Kv3 channels in FS neurons.

Co-expression of Kv3.4a and Kv3.1b cDNA in HEK293 cells produced $K^+$ currents with properties resembling those of Kv3 channels in FS neurons. The $K^+$ currents in co-transfected HEK293 cells activated rapidly at relatively negative membrane potentials and were efficiently activated by a spike waveform. These currents also were blocked at micromolar concentrations of TEA, as are Kv3 channel currents in neurons. Importantly, as predicted by the co-immunoprecipitation data, the biophysical features of currents in co-transfected cells could not be attributed to a sum of homomeric Kv3.1b and Kv3.4a channel currents. With strong depolarization, currents activated rapidly and then inactivated (n=9). In most cells (67%), inactivation had a fast component, in addition to a ubiquitous slow component. In these cells, the fast inactivation time constant was 38±9 msec (52±4% of total peak current at +10 mV), or about twice that seen with Kv3.4a homomeric channels at the same membrane potential. Although dissimilar to that of homomeric channel currents, this time constant is very close to that seen in FS GP neurons at similar potentials (38±8 ms; 38±3% of total current at +30 mV, n=5).

To determine if this resemblance extended to activation voltage dependence, two types of measurement were taken. First, peak currents were measured, converted to conductance and plotted as a function of step voltage. Second, tail currents were measured at the end of the 200 msec voltage step. At this time point, homomeric K3.4a channels have completely inactivated and do not contribute any detectable tail current. If the currents in these cells were simply a sum of currents arising from Kv3.4a and Kv3.1b homomers, then the peak and tail conductance plots should differ dramatically. Yet both measures of voltage dependence yielded very similar relative conductance plots, demonstrating that channels with novel properties were created by co-expression of these subunits. Moreover, these new channels had an activation voltage dependence that was indistinguishable from that of native Kv3 channels.

Another important feature of heteromeric channels was that they activated rapidly and deactivated nearly as fast as Kv3.1b homomeric channel currents. The combination of relatively low threshold of activation and rapid kinetics led to very efficient activation by the action potential waveform. On average, the repolarizing efficiency of the heteromeric Kv3.4a/Kv3.1b channels was 0.43±0.04 (n=7), compared to 0.42 for Kv3 channels in FS neurons and 0.09 for Kv3.1b channels.

To provide additional evidence that heteromeric channels were formed by co-expression of Kv3.1b and Kv3.4a subunits, single channel recordings were performed. In response to membrane depolarization, homomeric Kv3.4a channels displayed short openings with a mean open time of 8.05±0.50 ms (n=5). The slope conductance for these channels was 21.0+±3.5 pS (n=5). In contrast, homomeric Kv3.1b channels displayed long opening bursts interrupted by very brief closures (n=9). The slope conductance of these channels was 22.5±5.0 pS (n=5). Channels in cells co-expressing Kv3.1b and Kv3.4a subunits had short and long bursts of openings with the mean burst durations of 16.2±4.03 ms (33±10% of all bursts) and 250±50 ms, respectively (n=11). In spite of the similarity in the amplitude at +40 mV, the slope conductance of Kv3.4a/Kv3.1b channels was smaller than that of Kv3.1b channels (12.8±3.3 pS; n=5). Ensemble averages were compiled from 30 successive sweeps to compare the kinetic features of single channels with those of whole cell currents. The results show that there was a very clear correlation in the kinetics of current decay in the ensemble averages and those found in whole cell recordings. The decay time constant of Kv3.4a channel currents was similar to the single channel open time, while the decay of Kv3.1b and Kv3.4a/Kv3.1b currents was strongly correlated with burst duration. These data corroborate the inference that co-expression of Kv3.1b and Kv3.4a subunits leads to the formation of a heteromeric channel with distinctive properties.

The data described in Examples 2, 3, and 4 show 1) that several types of FS neuron co-express Kv3.4a and Kv3.1 mRNA, 2) that these two subunits co-assemble in rat brain and HEK293 cells, and 3) that Kv3.4a and Kv3.1b heteromeric channels are formed in HEK293 cells and these channels capture the key features of native Kv3 channels in FS neurons. Although strongly suggestive, these results do not show directly that Kv3.1 channels incorporate Kv3.4 subunits in FS neurons. To test this point, a pharmacological approach was taken.

EXAMPLE 5

The Kv3.4 Selective Toxin, BDS-I, Blocks Kv3 Currents in FS Neurons

At low micromolar concentrations, the sea anemone toxin BDS-I blocks homomeric Kv3.4 channels with only minor effects on Kv3.1 channel currents[17]. In FS neurons, BDS-I slowed the rising phase of delayed rectifier currents evoked by depolarization and reduced their amplitude, suggesting that Kv3.4a subunits contributed to channels underlying these currents.

To kinetically identify these channels, currents evoked in the presence of BDS-I were subtracted from control currents. If BDS-I simply eliminated currents through channels containing Kv3.4 subunits, the subtracted traces should resemble either homomeric Kv3.4 or heteromeric Kv3.4/Kv3.1 channel currents. The results indicated that the subtracted currents did not resemble currents arising from either channel type. With modest depolarization (−10 mV), the subtracted (difference) currents appeared slowly inactivating, whereas with stronger depolarization (+20 mV) the subtracted currents quickly decayed. Similar results were seen in every GP neuron tested (n=6).

To gain a better idea of how BDS-I was acting, it was applied to homomeric Kv3.4a channels expressed in HEK293 cells. In this case, the toxin slowed the rising phase of the currents but led to larger currents later in the step (n=5). This 'cross-over' blocking pattern is reminiscent of the voltage-dependent block of Kv4 A-type channels by 4-aminopyridine[18,19] where initially blocked channels unblock with sustained depolarization. As predicted by this model, the BDS-I block of Kv3.4a/Kv3.1b heteromeric channels in HEK293 cells was strong at the beginning of a depolarizing step and then waned with maintained depolarization (n=4).

This interpretation also is consistent with the apparent inactivation recovery kinetics of the BDS-I sensitive current in GP neurons. In both heterologous and native expression systems, Kv3 channels take seconds to recover from inactivation produced by strong depolarization[15,16]. As observed for Kv3 channels in GP neurons, as in heterologous systems, deinactivation of TEA-sensitive, Kv3 currents at −60 mV was slow, taking seconds. In contrast, the major component of the BDS-I difference currents recovered nearly two orders of magnitude faster, taking less than a second at −60 mV. If these currents were attributable to rapidly inactivating, homomeric, Kv3.4a channels, the recovery should have been slow. Rather, the rapid decay of currents during the conditioning step is attributable to the unbinding of BDS-I from channels containing Kv3.4 subunits; with repolarization, these channels re-block, leading to a progressive increase in the difference currents and a spurious recovery when the subtraction is performed. The speed of re-block is similar to that seen initially when BDS-I is applied using a rapid perfusion system. The slower component of this block is attributable to unblocking during test pulse, as its magnitude was diminished by decreasing the rate at which the test pulse was delivered.

Taken together, these results suggest that the subunit composition of Kv3 channels in GP neurons include Kv3.4 subunits. Although the voltage dependence of the BDS-I block precludes an accurate determination of the kinetic signature of native channels containing Kv3.4 subunits, it is clear that these channels do not inactivate rapidly, as do Kv3.4 homomeric channels. This is best illustrated in experimental results where the BDS-I subtraction yielded slowly decaying currents with moderate depolarizations, consistent with the proposition that Kv3.1 subunits in FS neurons form heteromers with Kv3.4 subunits.

Because it takes more than 5 msec at +20 mV for substantial unblocking, and because re-blocking is fast at potentials below spike threshold (ca. −60 mV), BDS-I should function as an effective blocker of channels containing Kv3.4 subunits during repetitive spiking. Indeed, BDS-I substantially broadened spikes in FS neurons, much as submillimolar concentrations of TEA have been shown to in previous studies 13. On average, the duration of spikes in FS neurons increased 53+13% in the presence of BDS-I (2 µM) and extracellular $Ca^{2+}$ (2 mM; to allow activation of $Ca^{2+}$ activated $K^+$ channels) (n=4). BDS-I produced no obvious change in the rate of rise in the spike and didn't significantly alter the inactivation kinetics of $Na^+$ currents in FS neurons (n=3, cf., [17]). In addition, BDS-I slowed the rate of repetitive spiking evoked by sustained current injection in FS neurons, in much the same way as selective block of Kv3 channels by TEA in cortical interneurons[13]. Similar results were seen in three neurons examined with extracellular $Ca^{2+}$ and in eight of nine FS neurons recorded in the absence of extracellular $Ca^{2+}$. Altogether, the BDS-I data show that a functionally important subset of Kv3 channels in FS neurons, if not all, contain Kv3.4 subunits.

EXAMPLE 6

Gene Therapy

An siRNA construct that effectively and selectively suppresses Kv3.4a mRNA levels in HEK293 cells stably expressing Kv3.1b and Kv3.4a mRNAs is developed first. The siRNA target is the 62 bp sequence absent in the Kv3.4c variant, or the sequences from position 2222-2283, where the sequence for Kv3.4a is in Gene Bank under accession number X62841.

The siRNA construct is then packaged in a viral delivery system for expression in a mouse model. A third-generation, replication deficient lentivirus vector with a biscistronic GFP construct is contemplated to be suitable for this purpose. Once packaged, the Kv3.4 siRNA containing lentivirus is stereotaxically injected into the globus pallidus and subthalamic nucleus of C57B/L6 mice. The GP/STN from control (lenti-mis-sense siRNA/GFP) and experimental mice are examined at the tissue and single cell level for Kv3.4a expression using RT-PCR techniques. Electrophysiological measurements are taken from GP/STN neurons using whole cell recording in tissue slices with GFP expression as a marker of infection. It is contemplated that Kv3.4a expression, but not Kv3.1b expression, is suppressed by the siRNA construct. Moreover, in infected GP/STN neurons, maximum discharge rates are diminished, as is the ability to fire in bursts.

As an additional control, siRNA virus is injected into the striatum and the normalcy of the physiological properties of medium spiny neurons are determined, as Kv3.4 mRNA is not expressed in these cells.

The results of these studies are contemplated to demonstrate that siRNA targeted specifically to Kv3.4a mRNA result in suppression of only Kv3.4 expression and that in infected GP/STN neurons, maximum discharge rates are diminished, as is the ability to fire in bursts. The effects of transfecting neuronal cells in vivo are then examined in a primate model of PD (MPTP lesioned).

For example, mammalian cells expressing the potassium channel were tested with siRNA vectors. HEK 293/Kv3.4a cells were generated by stable transfection with a linearized form of pcDNA3/Kv3.4a (Baranauskas et al., Nat Neurosci., 6:258 (2003)), and geneticin selection of a single clone. Kv3.4 expression was confirmed by quantitative PCR and Western blotting. Four target sequences were chosen (#1, #2, #3, and #4, described in more detail below). HEK293/Kv3.4 cells were transfected with these siRNA. To monitor transfection efficiency fluorescein labeled luciferase GL2-F1 siRNA (Dharmacon) was used. In transfected cells, labeled duplexes are detectable as discrete punctate cytoplasmic dots (Holen et al., Nucleic Acids Res., 30:1757 (2002)). Transfection efficiency was 60%, probably, due to high passage number.

Real-time quantitative PCR employing SYBR green fluorescence detection was used to measure Kv3.4 cDNA abundance. As a control for the non-specific effects of siRNA duplexes, siRNA targeting Kv3.1 was used. The differences in the amount of extracted RNA were taken into account by normalization to $\beta$-actin. Variability in the amplification during PCR reactions was estimated by running five PCR reactions for the same cDNA sample. Control cDNA was obtained from the cells transfected with siRNA targeted to Kv3.1 while the second sample was obtained from the cells transfected with duplex targeted to site C of Kv3.4 mRNA. Though both samples of cDNA contained relatively high levels of Kv3.4 mRNA, the data clearly showed the difference of 0.7 cycle in the amplified signal between control and duplex #3 transfected cells Kv3.4 mRNA. This would translate into ~1.7 difference of the Kv3.4 mRNA levels, however, $\beta$-actin mRNA levels were also lower in duplex #3 transfected cells suggesting lower yield of total RNA. Therefore, the ratio Kv3.4 mRNA to $\beta$-actin mRNA was still reduced by ~30% and it was statistically significant. Normalization to transfection efficiency results into the estimated suppression by 50% of the levels of Kv3.4 mRNA in the transfected cells for the two tested duplexes (#3 and #4) while the other two tested duplexes were essentially inactive as well as the control duplex targeting Kv3.1 mRNA.

Experimental Methods:

RNA Interference

Twenty-one-nucleotide double-stranded RNAs were synthesized by Dharmacon (Lafayette, CO). The duplexes used had the following sequences targeting rat Kv3.4 (accession no. X62841): site A (target #1), GCGAAATGTGACG-GAGATC (SEQ ID NO:1), corresponding to the coding region 765-783 relative to the first nucleotide of the start codon; site B (target #2), GGAAACGAGCAGACTCCAA (SEQ ID NO:2) (position 1607-1625); site C (target #3), GCAGAATGGTGACGCTAAT (SEQ ID NO:3) (position 1626-1644); site D (target #4), GGCAGTGTTGAGC-CGAAAC (SEQ ID NO:4) (position 1825-1843). The targeting sequence of rat Kv3.1 (accession no. X62840) was CAGCCACTTCGACTATGAC (SEQ ID NO:5) (position 129-147 relative to the first nucleotide of the start codon).

Fluorescein labeled luciferase GL2-F1 siRNA duplex (Dharmacon, Lafayette, CO) is used as a control of transfection efficacy.

Cells are transfected with Oligofectamine reagent (Invitrogen, Carlsbad, Calif.). Cells are seeded in 12-well plates on the day before transfection. Opti-MEM I (100 µl) is mixed with 5 µl of 20 µM siRNA duplex. In a second tube, 10 µl of Opti-MEM I is incubated with 2 µl of Oligofectamine for 8 min at room temperature. The two mixtures above are combined, gently mixed, and incubated for another 20 min. at room temperature. The entire mixture is added to the cells in 0.4 ml of DMEM without antibiotics. Cells are assayed after 24-48 h transfection.

Lentivirus Packaging

Lentivirus is made by transfecting HEK293T cells with pLentilox3.7 plasmid and with packaging plasmids VSVG, RSV-REV and pMDL g/p RRE. Virus is concentrated and tittered, $5 \times 10^5$ viral particles are used to infect about $10^5$ neural stem cells or HEK 293/Kv3.4 cells. The neural stem cells are grown as neurospheres for 48 hrs after viral infection and then the dissociated cells are plated on PDL coated coverslips. Phenotypic analysis is done after 48 hrs.

Vector Injections

Lentiviral vectors are diluted in sterile 20% sucrose in PBS. Subjects receive unilateral injections of approximately 0.5 µl into the globus pallidus under stereotaxic guidance. Virus is injected by glass micropipettes at rate of 50 nl/min using a controlled pressure device (Picospritzer, General Valve Corporation). Titers for the Kv3.4 and control vector stocks are matched. Following injection, gel foam is inserted into the hole to control bleeding and the overlying skin sutured with non-absorbable sutures.

The following references may be cited in the accompanying patent application. The citations are indicated in the specification by a reference number.

1. Hodgkin, A. L. & Huxley, A. F. Currents carried by sodium and potassium ions through the membrane of the giant axon of *Loligo. J Physiol* 116, 449-472 (1952).
2. Hodgkin, A. L. & Huxley, A. F. The components of membrane conductance in the giant axon of Loligo. *J Physiol* 116, 473-496 (1952).
3. Rudy, B. & McBain, C. J. Kv3 channels: voltage-gated channels designed for high-frequency repetitive firing. *TINS* 24, 517-26 (2001).
4. Coetzee, W. A. et al. Molecular diversity of K+ channels. *Ann N Y Acad Sci* 868, 233-85 (1999).
5. Brew, H. M. & Forsythe, I. D. Two voltage-dependent K+ conductances with complementary functions in postsynaptic integration at a central auditory synapse. *J Neurosci* 15, 8011-22 (1995).
6. Du, J., Zhang, L., Weiser, M., Rudy, B. & McBain, C. J. Developmental expression and functional characterization of the potassium-channel subunit Kv3.1b in parvalbumin-containing interneurons of the rat hippocampus. *J Neurosci* 16, 506-18 (1996).
7. Lenz, S., Pemey, T. M., Qin, Y., Robbins, E. & Chesselet, M. F. GABA-ergic interneurons of the striatum express the Shaw-like potassium channel Kv3.1. *Synapse* 18, 55-66 (1994).
8. Weiser, M. et al. Differential expression of Shaw-related K+ channels in the rat central nervous system. *J Neurosci* 14, 949-72 (1994).
9. Weiser, M. et al. The potassium channel subunit KV3.1b is localized to somatic and axonal membranes of specific populations of CNS neurons. *J Neurosci* 15, 4298-314 (1995).
10. Martina, M., Schultz, J. H., Ehmke, H., Monyer, H. & Jonas, P. Functional and molecular differences between voltage-gated K+ channels of fast-spiking interneurons and pyramidal neurons of rat hippocampus. *J Neurosci* 18, 8111-25 (1998).
11. Baranauskas, G., Tkatch, T. & Surmeier, D. J. Delayed rectifier currents in rat globus pallidus neurons are attributable to Kv2.1 and Kv3.1/3.2 K+ channels. *J Neurosci* 19, 6394-404 (1999).
12. Vega-Saenz de Miera, E. et al. in *Hanbook of Membrane Channels* 41-78 (Academic Press, Inc, 1994).

13. Erisir, A., Lau, D., Rudy, B. & Leonard, C. S. Function of specific K(+) channels in sustained high-frequency firing of fast-spiking neocortical interneurons. *J Neurophysiol* 82, 2476-89 (1999).
14. Wigmore, M. A. & Lacey, M. G. A Kv3-like persistent, outwardly rectifying, Cs+-permeable, K+ current in rat subthalamic nucleus neurones. *J Physiol* 527 Pt 3, 493-506 (2000).
15. Schroter, K. H. et al. Cloning and functional expression of a TEA-sensitive A-type potassium channel from rat brain. *FEBS Lett* 278, 211-6 (1991).
16. Rettig, J. et al. Characterization of a Shaw-related potassium channel family in rat brain. *Embo J* 11, 2473-86 (1992).
17. Diochot, S., Schweitz, H., Beress, L. & Lazdunski, M. Sea anemone peptides with a specific blocking activity against the fast inactivating potassium channel Kv3.4. *J Biol Chem* 273, 6744-9 (1998).
18. Thompson, S. Aminopyridine block of transient potassium current. *J Gen Physiol* 80, 1-18 (1982).
19. Song, W. J. et al. Somatodendritic depolarization-activated potassium currents in rat neostriatal cholinergic interneurons are predominantly of the A type and attributable to coexpression of Kv4.2 and Kv4.1 subunits. *J Neurosci* 18, 3124-37 (1998).
20. Kofuji, P., Davidson, N. & Lester, H. A. Evidence that neuronal G-protein-gated inwardly rectifying K+ channels are activated by G beta gamma subunits and function as heteromultimers. *Proc Natl Acad Sci USA* 92, 6542-6 (1995).
21. Sheng, M., Liao, Y. J., Jan, Y. N. & Jan, L. Y. Presynaptic A-current based on heteromultimeric K+ channels detected in vivo. *Nature* 365, 72-5 (1993).
22. Wang, H. S. et al. KCNQ2 and KCNQ3 potassium channel subunits: molecular correlates of the M-channel [see comments]. *Science* 282, 1890-3 (1998).
23. Abbott, G. W. et al. MiRP2 forms potassium channels in skeletal muscle with Kv3.4 and is associated with periodic paralysis. *Cell* 104, 217-31 (2001).
24. Macica, C. M. & Kaczmarek, L. K. Casein kinase 2 determines the voltage dependence of the Kv3.1 channel in auditory neurons and transfected cells. J Neurosci 21, 1160-8 (2001).
25. Murakoshi, H., Shi, G., Scannevin, R. H. & Trimmer, J. S. Phosphorylation of the Kv2.1 K+ channel alters voltage-dependent activation. *Mol Pharmacol* 52, 821-8 (1997).
26. Rettig, J. et al. Inactivation properties of voltage-gated K+ channels altered by presence of beta-subunit. *Nature* 369, 289-94 (1994).
27. Surmeier, D. J., Bargas, J., Hemmings, H. C., Jr., Naim, A. C. & Greengard, P. Modulation of calcium currents by a D1 dopaminergic protein kinase/phosphatase cascade in rat neostriatal neurons. *Neuron* 14, 385-97 (1995).
28. Hamill, O. P., Marty, A., Neher, E., Sakmann, B. & Sigworth, F. J. Improved patch-clamp techniques for high-resolution current recording from cells and cell-free membrane patches. *Pflugers Arch* 391, 85-100 (1981).
29. Yan, Z. & Surmeier, D. J. Muscarinic (m2/m4) receptors reduce N- and P-type Ca2+ currents in rat neostriatal cholinergic interneurons through a fast, membrane-delimited, G-protein pathway. *J Neurosci* 16, 2592-604 (1996).
30. Tkatch, T., Baranauskas, G. & Surmeier, D. J. Basal forebrain neurons adjacent to the globus pallidus co-express GABAergic and cholinergic marker mRNAs. *Neuroreport* 9, 1935-9 (1998).
31. Rhodes, K. J. et al. Association and colocalization of the Kvbeta1 and Kvbeta2 beta-subunits with Kv1 alpha-subunits in mammalian brain K+ channel complexes. *J Neurosci* 17, 8246-58 (1997).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A method of manipulating neuronal ion channels, comprising: transfecting a fast-spiking neuronal cell, wherein said fast spiking neuronal cell is capable of sustained high frequency discharge without significant accommodation, and wherein said cell comprises a co-assembled complex of mammalian Kv3.1, Kv3.2, Kv3.3 and Kv3.4, with a vector encoding an siRNA directed against an mRNA encoding a mammalian Kv3.4 protein wherein said siRNA is capable of inhibiting Kv3.4 expression in said cell, and wherein said inhibition of Kv3.4 expression results in a decrease in said sustained high frequency discharge in said cell but not in cells lacking said co-assembled complex.

2. The method of claim 1, further comprising the step of transplanting said cell into a subject.

3. The method of claim 1, wherein said frequency is greater than 100 Hz.

4. The method of claim 1, wherein said frequency is greater than 150 Hz.

5. The method of claim 1, wherein said mammalian Kv3.4 is rat.

6. The method of claim 1, wherein said mammalian Kv3.4 is human.

7. A method of manipulating neuronal ion channels, comprising: transfecting a fast-spiking neuronal cell, wherein said fast spiking neuronal cell is capable of sustained high frequency discharge without significant accommodation, and wherein said cell comprises a co-assembled complex of mammalian Kv3.1, Kv3.2, Kv3.3 and Kv3.4, with a vector encoding an siRNA having a nucleic acid selected from the group consisting of SEQ ID NOs: 3 and 4, wherein said siRNA is capable of inhibiting Kv3.4 expression in said cell, and wherein said inhibition of Kv3.4 expression results in a decrease in said sustained high frequency discharge in said cell but not in cells lacking said co-assembled complex.

8. A method of treating Parkinson's disease in a subject, comprising transfecting a fast-spiking neuronal cell, wherein said fast spiking neuronal cell is capable of sustained high frequency discharge without significant accommodation, and wherein said cell comprises a co-assembled complex of mammalian Kv3.1, Kv3.2, Kv3.3 and Kv3.4, and wherein said cell is in a subject diagnosed with Parkinson's disease, with a vector encoding an siRNA directed against an mRNA encoding a mammalian Kv3.4 protein wherein said siRNA is capable of inhibiting Kv3.4 expression in said cell, and wherein said inhibition of Kv3.4 expression results in a decrease in said sustained high frequency discharge in said cell but not in cells lacking said co-assembled complex.

* * * * *